(12) United States Patent
Zhao et al.

(10) Patent No.: US 12,398,366 B1
(45) Date of Patent: Aug. 26, 2025

(54) LACTICASEIBACILLUS RHAMNOSUS AFY01 AND APPLICATION OF PRODUCT PREPARED FROM LACTICASEIBACILLUS RHAMNOSUS AFY01 IN INFLAMMATORY COLON CANCER

(71) Applicant: Chongqing University of Education, Chongqing (CN)

(72) Inventors: Xin Zhao, Chongqing (CN); Fang Tan, Chongqing (CN); Xin Ma, Chongqing (CN); Xueping Yu, Chongqing (CN); Xingyao Long, Chongqing (CN); Yang Yu, Chongqing (CN)

(73) Assignee: Chongqing University of Education, Chongqing (CN)

( * ) Notice: Subject to any disclaimer, the term of this patent is extended or adjusted under 35 U.S.C. 154(b) by 0 days.

(21) Appl. No.: 19/021,675

(22) Filed: Jan. 15, 2025

Related U.S. Application Data

(63) Continuation of application No. PCT/CN2024/097495, filed on Jun. 5, 2024.

(30) Foreign Application Priority Data

Apr. 1, 2024 (CN) .......................... 202410383380.5

(51) Int. Cl.
| | | |
|---|---|---|
| *C12N 1/20* | (2006.01) | |
| *A61K 35/744* | (2015.01) | |
| *A61P 35/00* | (2006.01) | |
| *A61K 35/00* | (2006.01) | |
| *C12R 1/01* | (2006.01) | |

(52) U.S. Cl.
CPC ............ *C12N 1/205* (2021.05); *A61K 35/744* (2013.01); *A61P 35/00* (2018.01); *C12N 1/20* (2013.01); *A61K 2035/115* (2013.01); *C12R 2001/01* (2021.05)

(58) Field of Classification Search
CPC .......................... A61K 35/744; A61K 2035/115
See application file for complete search history.

(56) References Cited

FOREIGN PATENT DOCUMENTS

| | | |
|---|---|---|
| CN | 117264814 A | 12/2023 |
| CN | 117511811 A | 2/2024 |
| WO | 2021182829 A1 | 9/2021 |

OTHER PUBLICATIONS

Gamallet et al. Biomedicine & Pharmacotherapy 83 (2016) 536-541 (Year: 2016).*
Goldin et al. Nutrition and Cancer, 1996, vol. 25, Issue 2, pp. 197-204 (Year: 1996).*
International Search Authority (CNIPA), Written Opinion by the International Search Authority for PCT/CN2024/097495, Dec. 23, 2024.
Claims of PCT/CN2024/097495, Jun. 5, 2024.

\* cited by examiner

*Primary Examiner* — Melenie L Gordon
*Assistant Examiner* — Jessica Faye Edwards
(74) *Attorney, Agent, or Firm* — Hemisphere Law, PLLC; Zhigang Ma

(57) ABSTRACT

*Lacticaseibacillus rhamnosus* AFY01 and an application of a product prepared from *Lacticaseibacillus rhamnosus* AFY01 in inflammatory colon cancer are provided, which relates the field of microbes. A preservation number of the *Lacticaseibacillus rhamnosus* AFY01 is CGMCC No. 27362. The *Lacticaseibacillus rhamnosus* AFY01 can effectively alleviate weight loss, intestinal inflammation and edema induced colon shortening in mice with colon cancer, reduce colon coefficient, visceral index and incidence of intestinal tumors in mice, improve intestinal inflammation, promote apoptosis of intestinal tumor cells to slow down the development of colon cancer. The *Lacticaseibacillus rhamnosus* AFY01 expands bacterial resources to provide technical support for the prevention and treatment of colorectal cancer.

2 Claims, 30 Drawing Sheets
Specification includes a Sequence Listing.

```
                            SEQUENCE LISTING

Sequence total quantity: 20
SEQ ID NO: 1            moltype = DNA   length = 20
FEATURE                 Location/Qualifiers
source                  1..20
                        mol_type = other DNA
                        organism = synthetic construct
SEQUENCE: 1
agagtttgat cctggctcag                                                   20

SEQ ID NO: 2            moltype = DNA   length = 20
FEATURE                 Location/Qualifiers
source                  1..20
                        mol_type = other DNA
                        organism = synthetic construct
SEQUENCE: 2
ctacggctac cttgttacga                                                   20

SEQ ID NO: 3            moltype = DNA   length = 20
FEATURE                 Location/Qualifiers
source                  1..20
                        mol_type = other DNA
                        organism = synthetic construct
SEQUENCE: 3
tgtcagtcat cgcccatgtg                                                   20

SEQ ID NO: 4            moltype = DNA   length = 21
FEATURE                 Location/Qualifiers
source                  1..21
                        mol_type = other DNA
                        organism = synthetic construct
SEQUENCE: 4
catccttgcg agtgtcagtg a                                                 21

SEQ ID NO: 5            moltype = DNA   length = 21
FEATURE                 Location/Qualifiers
source                  1..21
                        mol_type = other DNA
                        organism = synthetic construct
SEQUENCE: 5
gacatcgcat cggctcttag a                                                 21

SEQ ID NO: 6            moltype = DNA   length = 21
FEATURE                 Location/Qualifiers
source                  1..21
                        mol_type = other DNA
                        organism = synthetic construct
SEQUENCE: 6
aacggtcacg gtgtacttct g                                                 21

SEQ ID NO: 7            moltype = DNA   length = 20
FEATURE                 Location/Qualifiers
source                  1..20
                        mol_type = other DNA
                        organism = synthetic construct
SEQUENCE: 7
actgccggga tggctactat                                                   20

SEQ ID NO: 8            moltype = DNA   length = 21
FEATURE                 Location/Qualifiers
source                  1..21
                        mol_type = other DNA
                        organism = synthetic construct
SEQUENCE: 8
tctggattcg ctggctaatg g                                                 21

SEQ ID NO: 9            moltype = DNA   length = 20
FEATURE                 Location/Qualifiers
source                  1..20
                        mol_type = other DNA
                        organism = synthetic construct
SEQUENCE: 9
agagggatt tcgattccgc                                                    20
```

-continued

```
SEQ ID NO: 10              moltype = DNA   length = 23
FEATURE                    Location/Qualifiers
source                     1..23
                           mol_type = other DNA
                           organism = synthetic construct
SEQUENCE: 10
cctgtgggta ggatttcttg ttc                                                23

SEQ ID NO: 11              moltype = DNA   length = 21
FEATURE                    Location/Qualifiers
source                     1..21
                           mol_type = other DNA
                           organism = synthetic construct
SEQUENCE: 11
tggcatcccc gaatatgatg a                                                  21

SEQ ID NO: 12              moltype = DNA   length = 22
FEATURE                    Location/Qualifiers
source                     1..22
                           mol_type = other DNA
                           organism = synthetic construct
SEQUENCE: 12
tgacagtagg ataggtcttc cg                                                 22

SEQ ID NO: 13              moltype = DNA   length = 20
FEATURE                    Location/Qualifiers
source                     1..20
                           mol_type = other DNA
                           organism = synthetic construct
SEQUENCE: 13
ccagtcacgc accatctttg                                                    20

SEQ ID NO: 14              moltype = DNA   length = 23
FEATURE                    Location/Qualifiers
source                     1..23
                           mol_type = other DNA
                           organism = synthetic construct
SEQUENCE: 14
gtccatctcg tttctaacca agt                                                23

SEQ ID NO: 15              moltype = DNA   length = 21
FEATURE                    Location/Qualifiers
source                     1..21
                           mol_type = other DNA
                           organism = synthetic construct
SEQUENCE: 15
gagagcgtca acagggagat g                                                  21

SEQ ID NO: 16              moltype = DNA   length = 20
FEATURE                    Location/Qualifiers
source                     1..20
                           mol_type = other DNA
                           organism = synthetic construct
SEQUENCE: 16
ccagcctccg ttatcctgga                                                    20

SEQ ID NO: 17              moltype = DNA   length = 21
FEATURE                    Location/Qualifiers
source                     1..21
                           mol_type = other DNA
                           organism = synthetic construct
SEQUENCE: 17
agcgtagaca aggagatgca g                                                  21

SEQ ID NO: 18              moltype = DNA   length = 22
FEATURE                    Location/Qualifiers
source                     1..22
                           mol_type = other DNA
                           organism = synthetic construct
SEQUENCE: 18
ccaaggctct aggtggtcat tc                                                 22

SEQ ID NO: 19              moltype = DNA   length = 21
FEATURE                    Location/Qualifiers
source                     1..21
                           mol_type = other DNA
                           organism = synthetic construct
SEQUENCE: 19
caacttccta gactgcaacc g                                                  21
```

```
SEQ ID NO: 20          moltype = DNA  length = 21
FEATURE                Location/Qualifiers
source                 1..21
                       mol_type = other DNA
                       organism = synthetic construct
SEQUENCE: 20
tccaactcgc tcacttcttc t                                         21
```

LACTICASEIBACILLUS RHAMNOSUS AFY01 AND APPLICATION OF PRODUCT PREPARED FROM LACTICASEIBACILLUS RHAMNOSUS AFY01 IN INFLAMMATORY COLON CANCER

TECHNICAL FIELD

The disclosure belongs to the microbial field, and particularly relates to *Lacticaseibacillus rhamnosus* AFY01 and an application of a product prepared from *Lacticaseibacillus rhamnosus* AFY01 in inflammatory colon cancer.

STATEMENT REGARDING SEQUENCE LISTING

The sequence listing associated with this application is provided in text format in lieu of a paper copy and is hereby incorporated by reference into the specification. The name of the XML file containing the sequence listing is 25007TLAN-USP1-SL.xml. The XML file is 18,812 bytes; is created on Jan. 15, 2025; and is being submitted electronically via patent center.

BACKGROUND

Colon cancer is a common malignant tumor of the digestive tract that occurs in the colon. The pathogenesis of the colon cancer is complex and diverse, including environmental and dietary factors, personal habits, and familial and hereditary factors. Chronic inflammation is also recognized as an important risk factor for a variety of cancers, and the degree of chronic intestinal inflammation is positively correlated with occurrence of intestinal tumors, which has a promoting effect on the development of inflammation-related colon cancer. In order to explore the pathological mechanism of the colon cancer and simulate the pathological process of human colon cancer, multiple experimental animal models of the colon cancer have been developed. Among these models, the azoxymethane (AOM)/dextran sodium sulfate (DSS) model is a simple and reproducible animal model of colon cancer. As a carcinogen, AOM can trigger tumor formation, and DSS is a heparin-like polysaccharide that can cause damage to colonic epithelial cells, leading to intestinal inflammation. The main features of the AOM/DSS model are that modeling has high accuracy and a short cycle, and intestinal tumor development may occur within as short as 10 weeks. In addition, AOM/DSS-induced tumor histopathology can highly simulate the occurrence and development process of human colon cancer.

The pathophysiologic mechanism of the colon cancer is complex, and the development is a multi-stage process. A nuclear factor κB (NF-κB) signaling pathway plays a key role in the pathophysiology of colon cancer, affecting tumor initiation, progression and metastasis. Current evidence has showed that NF-κB-mediated transcription plays a crucial role in the development of the colon cancer as a major link between inflammation and cancer. Activation of the NF-κB signaling pathway promotes the establishment of a proinflammatory tumor microenvironment in the colon cancer and regulates the expression of target genes associated with cell proliferation, apoptosis, metastasis, angiogenesis, drug resistance, and inflammation. Furthermore, NF-κB is considered to be a major anti-apoptotic factor, which not only activates anti-apoptotic proteins (Bcl-2, Bcl-xL), but also inactivates the expression of pro-apoptotic proteins (Bid, Bax, Bak), and reduces the activity of caspases, thus inhibiting the apoptosis of colon cancer cells.

At present, commonly treatment drugs used by colon cancer patients include fluorouracil, irinotecan, oxaliplatin and raltitrexed, but these drugs are usually accompanied by certain side effects. A great deal of evidence shows that aspirin has a preventive effect on cancer, especially the colon cancer. However, clinical studies have found that the aspirin can cause a range of gastrointestinal side effects, and particularly can lead to upper gastrointestinal damage, including dyspepsia, peptic ulcer bleeding, and even death. Compared with drugs with side effects, probiotics, as natural microorganisms, are non-toxic and harmless, and more beneficial to the human body.

*Lactobacillus plantarum*, as a kind of lactic acid bacteria, widely exists in fermented dairy products, meat and vegetables, and as a probiotic group in the human gastrointestinal tract, the *Lactobacillus plantarum* has great promotion to human health. As a kind of edible lactic acid bacteria, *Lacticaseibacillus rhamnosus* exist in a human body and an environment, and provides a certain protection effect on normal cells and bodies while influencing the occurrence and development of the colon cancer. The *Lacticaseibacillus rhamnosus* can directly intervene in the occurrence and development of the colon cancer by regulating immunity, regulating cell stress response, inhibiting inflammation, regulating cell proliferation, apoptosis, pyroptosis and metastasis.

The patent CN117264814A provides *Lacticaseibacillus rhamnosus* having prophylactic and therapeutic effects on digestive tract diseases, and the preservation number is CGMCC No. 27362. This strain is resistant to gastric acids and bile salts, and can relieve antibiotic-induced diarrhea in mice. The strain has a preventive effect on DSS-induced colitis in mice. The strain can also alleviate AOM/DSS-induced colon cancer in mice.

In view of the high morbidity and mortality of the colon cancer, it is of great clinical significance to develop safer and more effective probiotics.

SUMMARY

In order to solve the above problems, the disclosure provides *Lacticaseibacillus rhamnosus* AFY01. AFY01 can effectively interfere with the establishment of a mouse inflammation-related colon cancer model through a chemical inducer AOM/DSS, has a good therapeutic effect on colon cancer, and provides screened candidate strains for developing probiotics targeting at the colon cancer.

In one aspect, the disclosure provides *Lacticaseibacillus rhamnosus* AFY01 with the preservation number of CGMCC No. 27362.

In another aspect, the disclosure provides a culture method for the *Lacticaseibacillus rhamnosus* AFY01 mentioned above, and the method includes inoculating the *Lacticaseibacillus rhamnosus* AFY01 onto a culture medium for culture, where the culture medium includes but not limited to an MRS culture medium.

In another aspect, the disclosure provides an application of the *Lacticaseibacillus rhamnosus* AFY01 in preparation of a product for prevention, treatment and/or adjuvant treatment of intestinal cancer.

Specifically, the product includes but not limited to: fermentation broth of the *Lacticaseibacillus rhamnosus* AFY01, supernatant of fermentation broth, precipitate of fermentation broth, viable bacteria and/or dead bacteria.

Further specifically, the fermentation broth refers to a liquid obtained by inoculating a strain onto a culture medium for culture for a period of time.

Further specifically, the supernatant of fermentation broth refers to a clarified liquid from an upper layer after centrifugation of the fermentation broth, and the supernatant contains abundant metabolites and partial thallus fragments in the growth and reproduction process of bacteria. Acidic substances and bacteriocins secreted by the bacteria have antagonistic and killing effects on harmful bacteria. Amino acids and synthetic vitamins after food decomposition by the bacteria are all in the culture liquid, and enzymes useful to a human body secreted by the bacteria are also included. Partial thallus components also have an immune promoting effect on the human body.

Further specifically, the precipitate of fermentation broth refers to liquid precipitate obtained through centrifugation, which includes free proteins, residual thalli, broken cells, and residues of a culture matrix, and mainly includes the proteins and matrices in cells.

Further specifically, the viable bacteria are also called an active flora, and can colonize and multiply in intestinal tracts, which is conductive to increase of the number of probiotics.

Further specifically, the dead bacteria refer to microorganisms which have lost the vitality and are unable to grow and reproduce, and the probiotics lose the vitality due to production processes such as high temperature treatment or excessive drying.

Specifically, the intestinal cancer is small intestine cancer, colon cancer and/or rectal cancer.

Optionally, the intestinal cancer is colon cancer.

In another aspect, the disclosure provides a product for prevention, treatment and/or adjuvant treatment of intestinal cancer, and the product includes the *Lacticaseibacillus rhamnosus* AFY01 mentioned above.

Specifically, the product is a drug, and the drug includes fermentation broth of the *Lacticaseibacillus rhamnosus* AFY01, supernatant of fermentation broth, precipitate of fermentation broth, viable bacteria and/or dead bacteria.

Further specifically, the drug includes viable bacteria of the *Lacticaseibacillus rhamnosus* AFY01, and the viable count is not less than $1\times10^8$ CFU/kg.

Optionally, the viable count of the *Lacticaseibacillus rhamnosus* AFY01 in the drug is $1\times10^8$ CFU/kg-$1\times10^{12}$ CFU/kg.

Further optionally, the viable count of the *Lacticaseibacillus rhamnosus* AFY01 in the drug is $1\times10^8$ CFU/kg to $1\times10^9$ CFU/kg, such as $1\times10^8$ CFU/kg, $2\times10^8$ CFU/kg, $3\times10^8$ CFU/kg, $4\times10^8$ CFU/kg, $5\times10^8$ CFU/kg, $6\times10^8$ CFU/kg, $7\times10^8$ CFU/kg, $8\times10^8$ CFU/kg and $9\times10^8$ CFU/kg. Other point values in this value range can be selected.

Further specifically, the drug further includes a pharmaceutically acceptable accessory.

More specifically, the pharmaceutically acceptable accessory is selected from one or a combination of more than two of wetting agents, emulsifiers, preservatives, antioxidants, buffering agents, excipients, diluents, lubricants, bacteriostats, suspending agents, suspending aids, solubilizers, thickeners, stabilizers, sweeteners and spices.

Optionally, the pharmaceutically acceptable accessory is at least one selected from lactose, mannose, starch, gum arabic, calcium phosphate, alginate, gelatin, calcium silicate, fine crystalline cellulose, polyvinylpyrrolidone, cellulose, water, syrup, methylcellulose, methyl hydroxybenzoate, propyl hydroxybenzoate, talc, magnesium stearate and mineral oil.

Further specifically, the dosage form of the drug can be powder, tablets, capsules or pills.

Specifically, the product is food, and the food includes fermentation broth of the *Lacticaseibacillus rhamnosus* AFY01, supernatant of fermentation broth, precipitate of fermentation broth, viable bacteria and/or dead bacteria.

Further specifically, the food includes an acceptable accessory for food.

More specifically, the acceptable accessory for food is selected from one or a combination of more than two of wetting agents, emulsifiers, suspension stabilizers, excipients, diluents, lubricants, preservatives, sweeteners and spices.

Optionally, the acceptable accessory for food is at least one selected from lactose, glucose, sucrose, sorbitol, mannose, starch, gum arabic, calcium phosphate, alginate, gelatin, calcium silicate, fine crystalline cellulose, polyvinylpyrrolidone, cellulose, water, syrup, methylcellulose, methyl hydroxybenzoate, propyl hydroxybenzoate, talc, magnesium stearate and mineral oil.

More specifically, the food includes but not limited to: tea juice, biscuits, drinks, coffee, soda, beverages, cakes, bread, mooncakes, dairy products, milk products, candies and/or chocolates.

Specifically, the product is a health care product, and the health care product includes fermentation broth of the *Lacticaseibacillus rhamnosus* AFY01, supernatant of fermentation broth, precipitate of fermentation broth, viable bacteria and/or dead bacteria.

Further specifically, the health care product includes an acceptable accessory for health care products.

More specifically, the accessory is selected from one or a combination of more than two of filler, capsule shell materials, solvents, stabilizers, excipients, sweeteners and pigments.

Optionally, the filler is selected from at least one of starch, corn flour, and grapes,
  the capsule shell material is selected from at least one of gelatin, hydroxypropyl methyl cellulose and polyvinyl alcohol,
  the solvent is selected from at least one of water, alcohol, glycerol and ethanol,
  the stabilizer is selected from at least one of an antioxidant and a preservative,
  the excipient is selected from at least one of natural spices and artificial essence,
  the sweetener is selected from at least one of a natural sweetener and an artificial sweetener, and
  the pigment is selected from at least one of a natural pigment and an artificial pigment.

The technical effects achieved through the disclosure are as follows:

(1) LR-AFY01 can effectively alleviates the phenomenon of pathological weight loss in mice.

(2) LR-AFY01 can effectively relieve colon shortening caused by intestinal inflammation edema, reduce colon coefficients of the mice, reduce visceral indexes and intestinal tumor occurrence of the mice.

(3) LR-AFY01 can effectively relieve pathological damage of colon tissue caused by AOM/DSS.

(4) LR-AFY01 can significantly reduce levels of proinflammatory cytokines (IL-1β, IL-6 and TNF-α) in mice with colon cancer, perform down regulation on the expression of NF-κB and iNOS, and alleviate the pathological state of inflammation.

(5) LR-AFY01 can perform significant down regulation on the mRNA expression of proinflammatory factors of IκBβ, p65, p50 and p52, and anti-apoptotic factors of Bcl-2 and Bcl-XL, and perform significant up regulation on the mRNA expression of the pro-apoptotic factors of Bid and caspase-8.

Preservation Description:
  Name of strain: AFY01;
  Preservation number: CGMCC No. 27362;
  Classification and naming: *Lacticaseibacillus rhamnosus*;
  Preservation date: May 17, 2023;
  Preservation institution: China General Microbiological Culture Collection Center; and
  Address of preservation institution: No. 3, Yard 1, Beichen West Road, Chaoyang District, Beijing.

The deposits were made and accepted under the Budapest Treaty and applicant avers under 37 CFR § 1.808 (a) that the deposit was made under conditions that assure that:
  (1) Access to the deposit will be available during pendency of the patent application making reference to the deposit to one determined by the Director to be entitled thereto under $1.14 and 35 U.S. C. § 122, and
  (2) Subject to paragraph (b) of this section, all restrictions imposed by the depositor on the availability to the public of the deposited material will be irrevocably removed upon the granting of the patent.

DETAILED DESCRIPTION OF THE EMBODIMENTS

Figure 1:
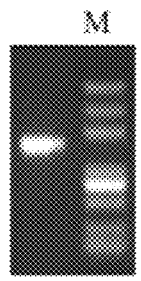
FIG. 1 shows gel electrophoresis results of genomic DNA amplification products of *Lacticaseibacillus rhamnosus* AFY01, where M is 5000 bp, 3000 bp, 2000 bp, 1000 bp, 750 bp, 500 bp, 250 bp and 100 bp in sequence from top to bottom.
Figure 2:
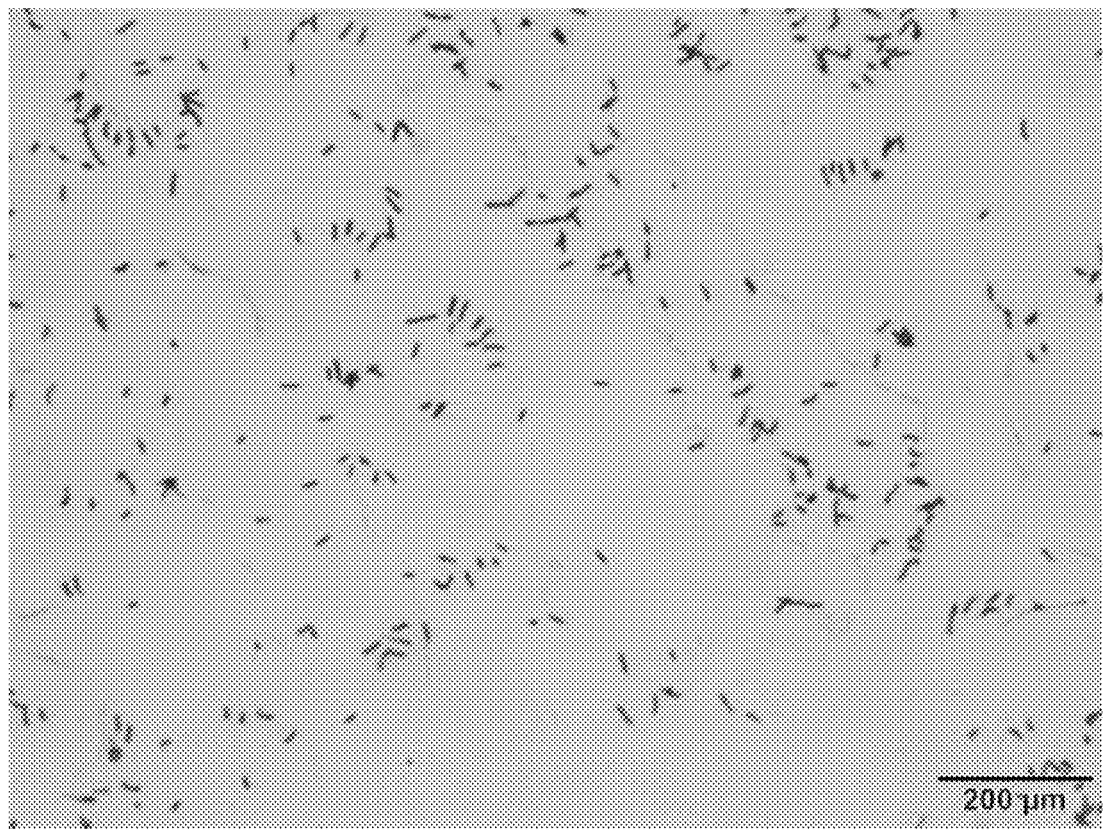
FIG. 2 is a gram staining microscopy image of *Lacticaseibacillus rhamnosus* AFY01.

The disclosure will be further described in detail below with reference to particular embodiments, and the following embodiments are not intended to limit the disclosure and are merely used for describing the disclosure. All experimental methods used in the following embodiments are conventional methods unless otherwise specified. Experimental methods are usually implemented according to conventional conditions if specific conditions are not specified. All used materials, reagents, etc. in the following embodiments may be obtained from a commercial approach unless otherwise specified.

*Lacticaseibacillus rhamnosus* AFY01 in the disclosure is referred to as LR-AFY01 or AFY01 for short.

Embodiment 1 Isolation, purification and identification of *Lacticaseibacillus rhamnosus* AFY01

Natural fermented yogurt from Altay Prefecture in Xinjiang is used. 40 mL of natural fermented yogurt is sucked into a sterile centrifuge tube, placed in a food sampling box, and stored in a refrigerator at 4° C. in a laboratory for later use.

1.1 Isolation and Identification 1.1.1 Isolation and Purification 1 mL of naturally fermented yogurt sample is taken and diluted at a 10-fold gradient to $10^{-6}$ with a stroke-physiological saline solution. Then, 100 μL of bacterial solutions at three gradients of $10^{-4}$, $10^{-5}$ and $10^{-6}$ for plate coating (MRS culture medium), and culture is carried out at 37° C. for 24-48 h. Colony morphology is observed and recorded. Streaking isolation is carried out by picking up colonies with different morphology from a plate. After culture at 37° C. for 48 h, single colonies with different morphology on the plate are picked up again for streaking isolation, and repetition is carried out twice to three times in this way until pure single colonies with consistent morphology are obtained.

The formula of the MRS culture medium is as follows: 10.0 g/L of peptone, 10.0 g/L of beef extract, 5.0 g/L of yeast, 20.0 g/L of glucose, 5.0 g/L of sodium acetate, 2.0 g/L of diamine hydrogen citrate, 1.0 mL/L of tween-80, 2.0 g/L of dipotassium hydrogen phosphate, 0.2 g/L of magnesium sulfate heptahydrate, 0.05 g/L of manganese sulfate heptahydrate and the balance distilled water.

1.1.2 DNA Extraction

The purified suspected target strain is inoculated into MRS broth and cultured at 37° C. for 18-24 h, and then, DNA extraction is carried out by using a bacterial genomic DNA extraction kit. The extracted DNA is numbered and stored in a freezer at −20° C. for later use.

1.1.3 PCR Amplification of Genomic DNA and Agarose Gel Electrophoresis Testing

PCR amplification is carried out on the extracted DNA, including 1 μL of forward primer 27F (SEQ ID NO. 1: 5'-AGA GTT TGATCCTGGCTC AG-3'), 1 μL of reverse primer 1495R (SEQ ID NO. 2: 5'-CTA CGGCTA CCTTGT-TACGA-3'), 12.5 μL of 2×Taq plus Buffer, and 1 μL of a template DNA, and the system is added to 25 μL through sterile dd H2O. Sterile ultrapure water is used for replacing the template DNA, which serves as a negative control. Amplification conditions are as follows: 94° C. for 5 min, 94° C. for 30 s, 55° C. for 30 s, 72° C. for 1 min, 29 cycles in total, and final extension at 72° C. for 5 min.

Then, 5 μL of amplified product are tested through agarose gel electrophoresis, where a concentration of agarose is 1.5%, and the electrophoresis conditions are 110 V and 45 min. PCR products passing the test are sent to BGI Genomics Co., Ltd. for sequencing, and alignment analysis is carried out on sequences subjected to successful sequencing through a BLAST (Basic Local Alignment Search Tool) program of NCBI.

1.2 In-Vitro Resistance Screening 1.2.1 Capacity of Tolerance to 0.3% Bile Salt

A porcine bile salt is added into a MRS-THIO culture medium (MRS broth containing 0.2% of sodium thioglycollate) to make a concentration of the bile salt be 0.3%, sterilization is carried out at 121° C. for 15 min, and 5 mL of activated strains are inoculated into a MRS-THIO culture medium without a bile salt (0.0%) and a MRS-THIO culture medium with 0.3% of a bile salt at an inoculation volume of 2% (v/v) respectively. A blank culture medium (not inoculated into a MRS-THIO culture medium) as a control. After culture at 37° C. for 24 h, OD 600 nm values of the above culture media with different concentrations are determined, and the tolerance of the strains to the bile salt is calculated according to Formula (1):

$$\text{Tolerance to bile salt (\%)} = \frac{\substack{OD600\text{nm of culture medium containing bile salt of } 0.3\% - \\ OD600\text{nm of blank culture medium}}}{OD600\text{nm of culture medium containing bile salt of } 0.0\% - OD600\text{nm of blank culture medium}} \times 100 \quad (1)$$

1.2.2 Tolerance Test of Artificial Gastric Juice

Preparation of artificial gastric juice: the artificial gastric juice is composed of 0.2% of NaCl and 0.35% of pepsin. According to the corresponding mass volume ratio, NaCl and pepsin required for the test are separately weighed for preparation. pH of the prepared artificial gastric juice is adjusted to 3.0 with HCl of 1 mol/L, and then filtered and sterilized with a 0.22 μm filter membrane for later use.

5 mL of cultured culture medium is sucked into a 10 mL sterile centrifuge tube on an ultra-clean workbench, centrifugation is carried out at 3000 r/min for 10 min, the culture medium on the upper layer is discarded, and bacteria are collected. An equal volume (5 mL) of stroke-physiological saline solution is added and mixed well to prepare a bacterial suspension. Then, 1 mL of the bacterial suspension is taken and mixed well with 9 mL of the artificial gastric juice with pH of 3.0. In this case, 1 mL of the above mixed solution is taken to serve as a sample with the artificial gastric juice treated for 0 h. The remaining 9 mL of the mixed solution is cultured in a constant-temperature water bath shaking table (37° C., 150 r/min) for 3 h. Samples treated for 0 h and 3 h each are diluted in a 10-fold gradient. The viable count is determined by a plate coating method at an appropriate gradient. Culture is carried out on a solid MRS culture medium at 37° C. for 48 h. a survival rate (%) is calculated according to Formula (2).

$$\text{Survival rate (\%)} = \frac{\text{Viable count for } 3\,h/(CFU/\text{mL})}{\text{Viable count for } 0\,h/(CFU/\text{mL})} \times 100 \quad (2)$$

1.3 Results and Analysis 1.3.1 PCR Amplification Product Sequencing and Gel Electrophoresis Results Results of agarose gel electrophoresis are shown in FIG. 1.

1.3.2 Species Analysis of Strain Through Gene Bank

Alignment analysis through the BLAST program shows that the isolated and purified strain is identified as the *Lacticaseibacillus rhamnosus*.

1.3.3 Results of *Lactobacillus* In-Vitro Resistance

Table 1 shows that *Lactobacillus fermentum* AFY01 has a high survival rate in the artificial gastric juice and strong bile salt tolerance.

TABLE 1

Survival rates of *Lactobacillus fermentum* AFY01 in artificial gastric juice with pH of 3.0 and bile salt of 0.3%

| Serial number of strain | Chinese name | Survival rate in artificial gastric juice with pH of 3.0 (%) | Survival rate in bile salt of 0.3% (%) |
|---|---|---|---|
| AFY01 | *Lacticaseibacillus rhamnosus* | 94.27% | 86.19% |

Embodiment 2

2.1 Materials and Regents

Isolation is carried out on naturally fermented yogurt from a herdsman's home in Altay Prefecture of Xinjiang, and a product is preserved in China General Microbiological Culture Collection Center with the preservation number of CGMCC No. 27362.

Azoxymethane (AOM) from Sigma Aldrich (Shanghai) Trading Co., Ltd. (Sigma-Aldrich); dextran sodium sulfate (DSS) from MP Biomedicals LLC, USA; aspirin enteric-coated tablets (national medicine permission number: HJ20160685, barcode: 6924147659034) from Bayer Healthcare Co., Ltd.; interleukin 6 (IL-6), interleukin 1β (IL-1β), tumor necrosis factor α (TNF-α), NF-κB, and inducible NO synthase (iNOS) ELISA kit from Shanghai Enzyme linked Biotechnology Co., Ltd.; RNase-Free water from Beijing Solarbio Science&Technology Co., Ltd.; qPCR SYBR Green Master Mix from Shanghai Yisheng Biotechnology Co., Ltd.; and TRIzol Reagent, and RevertAid First Strand cDNA Synthesis Kit from Thermo Fisher Scientific, USA. The rest reagents are domestic biochemical reagents or analytical reagents.

2.2 Instruments and Apparatuses

6D45415 upright microscope from Olympus Instruments Co., Ltd., Japan; Bioprep-24 biological sample homogenizer, and Nano-300 microspectrophotometer from Hangzhou Aosheng Instruments Co., Ltd.; A200 gradient PCR instrument from Hangzhou Langji Scientific Instruments Co., Ltd.; and VLBLOTD1 multifunctional microplate reader, and OneStepPlus Real-Time PCR System from Thermo Fisher Scientific (Suzhou) Co., Ltd.

2.3 Experimental Method 2.3.1 Design of Animal Experiment

C57BL/6 mice (SPF grade, male, 6 weeks old) are purchased from Hunan SJA Laboratory Animal Co., Ltd. [Animal Qualification License No.: SCXK (Xiang) 2019-0004] and are randomly divided into 5 groups after 7 days of adaptive feeding in a constant temperature and humidity environment, including a normal group, a model group, an aspirin group, a low-concentration LR-AFY01 (LR-AFY01L) group, and a high-concentration LR-AFY01 (LR-AFY01H) group. During the experiment, the mice are fed freely with food and water. The model group, the aspirin group and the LR-AFY01 groups are injected intraperitoneally with azoxymethane (AOM) at the concentration of 10 mg/kg on the first day of experiment modeling, and fed with a 2.5% DSS aqueous solution at the 2nd week, the 5th week and the 8th week respectively. Mice in the normal group are given a stroke-physiological saline solution daily without special treatment. Mice in the model group are given a stroke-physiological saline solution daily. Mice in the aspirin group are given an aspirin solution at 67 mg/kg. Mice in the LR-AFY01L group and mice in the LR-AFY01H group are given an LR-AFY01 bacterial suspension at $1\times10^8$ CFU/kg and $1\times10^9$ CFU/kg respectively for 10 weeks. During the experiment, the states of the mice in each group are observed, the mice are weighed, and the weights of the mice are recorded every week. After modeling is completed, the mice are killed through eyeball blood sampling and removal of vertebral columns, and colon tissue is dissected for testing.

A preparation method for the bacterial suspension is as follows: P2 generation strains are inoculated at an inoculation amount of 2% (100 μL) into 5 mL of MRS culture medium at a constant temperature of 36° C. for 16 hours, and then, gradient dilution is carried out. The concentration of a stock solution is calculated. Then, dilution is carried out to make the concentration be the doses of $1\times10^8$ CFU/kg and $1\times10^9$ CFU/kg according to needs, where a diluent used for dilution is distilled water.

2.3.2 Determination of Visceral Index and Colon Coefficient

The colon tissue of the experimental mice is weighed, and the visceral indexes of the mice are calculated according to the following formula: visceral index=visceral weight (g)/mouse weight (g)×100. At the same time, the colon lengths of the mice are measured, and the occurrence of intestinal tumors is observed. The colon coefficients of mice are calculated, and the colon coefficient=colon weight (mg)/colon length (cm).

2.3.3 Pathological Observation of Colon Tissue

The colon tissue of about 0.5 cm in length is immersed in a 4% paraformaldehyde fixing solution for 48 h, dehydrated with ethanol and embedded in paraffin, cut into sections of about 2-3 μm with a microtome, stained with hematoxylin and eosin (H&E) and fixed on glass slides, i.e., made into pathological sections of mouse colon, and observed morphological changes under an upright microscope.

2.3.4 Level Determination of Inflammation-Associated Factors in Serum and Colon Tissue of Mice The whole blood samples of mice are collected and centrifuged at 4000 r/min for 10 min at 4° C. to obtain serum. Levels of IL-6, IL-1β, TNF-α, NF-κB and iNOS in serum and colon tissue of the mice are determined according to the instructions of an enzyme linked immunosorbent assay (ELISA) kit.

2.3.5 Determination of Expression Levels of Genes Related to Inflammation and Apoptosis Pathways in Colon Tissue of Mice 50 mg of colon tissue of the mice is weighed, the total RNA is extracted through a TRIzol reagent, and is reversely transcribed into a cDNA according to the instructions provided in a cDNA synthesis kit. The concentration and purity of the RNA and the cDNA are determined by using a microphotometer. Amplification is performed for 40 cycles by using a StepOnePlus Real-Time PCR system under the following conditions: keeping at 95° C. for 15 s, denaturation at 60° C. for 30 s, keeping at 95° C. for 15 s, keeping at 60° C. for 60 s, and denaturation at 95° C. for 15 s. The relative expression intensity of each gene is calculated by a $2^{-\Delta\Delta Ct}$ method with Eef2 as an internal reference gene. Primer sequences used in this experiment are shown in Table 2.

TABLE 2

Primer sequence

| Name of primer | GenBank accession numbers | Primer sequence (5'-3') |
|---|---|---|
| Eef2 | NM_007907.2 | F(SEQ ID NO. 3): TGTCAGTCATCGCCCATGTG<br>R(SEQ ID NO. 4): CATCCTTGCGAGTGTCAGTGA |
| IκBβ | NM_010546.2 | F(SEQ ID NO. 5): GACATCGCATCGGCTCTTAGA<br>R(SEQ ID NO. 6): AACGGTCACGGTGTACTTCTG |
| p65 | NM_009045.4 | F(SEQ ID NO. 7): ACTGCCGGGATGGCTACTAT<br>R(SEQ ID NO. 8): TCTGGATTCGCTGGCTAATGG |
| p50 | NM_008689.3 | F(SEQ ID NO. 9): AGAGGGGATTTCGATTCCGC<br>R(SEQ ID NO. 10): CCTGTGGGTAGGATTTCTTGTTC |
| p52 | NM_001177370.1 | F(SEQ ID NO. 11): TGGCATCCCCGAATATGATGA<br>R(SEQ ID NO. 12): TGACAGTAGGATAGGTCTTCCG |
| Bid | NM_007544.4 | F(SEQ ID NO. 13): CCAGTCACGCACCATCTTTG<br>R(SEQ ID NO. 14): GTCCATCTCGTTTCTAACCAAGT |
| Bcl-2 | NM_177410.3 | F(SEQ ID NO. 15): GAGAGCGTCAACAGGGAGATG<br>R(SEQ ID NO. 16): CCAGCCTCCGTTATCCTGGA |
| Bcl-xL | NM_009743.5 | F(SEQ ID NO. 17): AGCGTAGACAAGGAGATGCAG<br>R(SEQ ID NO. 18): CCAAGGCTCTAGGTGGTCATTC |
| caspase-8 | NM_009812.2 | F(SEQ ID NO. 19): CAACTTCCTAGACTGCAACCG<br>R(SEQ ID NO. 20): TCCAACTCGCTCACTTCTTCT |

2.4 Data Analysis

All data are expressed as mean±stand deviation (mean±SD), and one-way ANOVA in IBM SPSS 27.0 is used for significance analysis. GraphPad 9.3.1 is used for plotting, and different letters a-d in the graph indicate that the difference is statistically significant through a Duncan multi-range test (P<0.05).

2.5 Results and Analysis 2.5.1 Influence of LR-AFY01 on Weight of Mice

Figure 3:
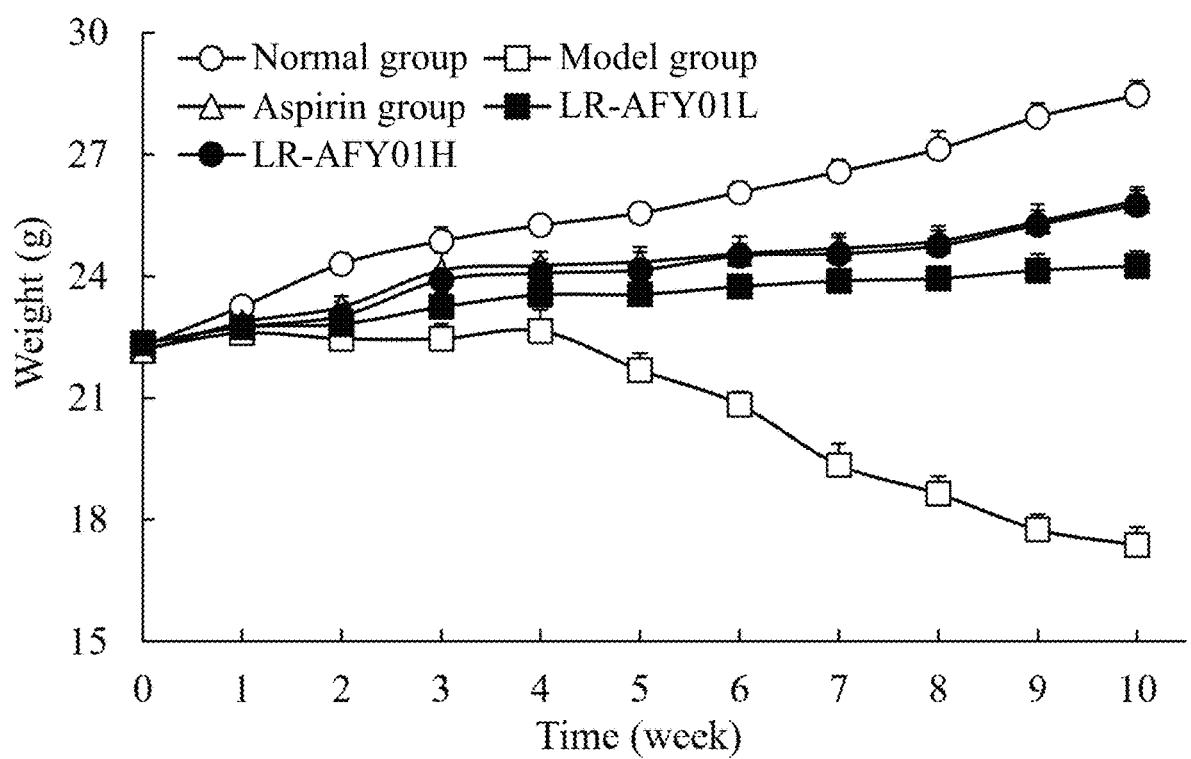
FIG. 3 shows influence of *Lacticaseibacillus rhamnosus* AFY01 on weights of mice.

During the modeling process of the disclosure, it is observed that the mice in the normal group have healthy physique, eating and drinking are normally, and no diarrhea and hematochezia occur, while the mice in the other 4 groups have symptoms such as incomplete stool, hematochezia, and even anal prolapse in different degrees, and meanwhile, the conditions such as reduced activity ability, sparse and lustrous hair color, and weight loss occur. As shown in FIG. 3, the weight of mice in the normal group show an increasing trend, while the weight of mice in other 4 groups show a decreasing trend after each feeding of the DSS aqueous solution, and the weight of mice in each group has significant difference (P<0.05). After aspirin and LR-AFY01 intervention, the pathological weight loss trend of mice is obviously alleviated.

Figure 4:
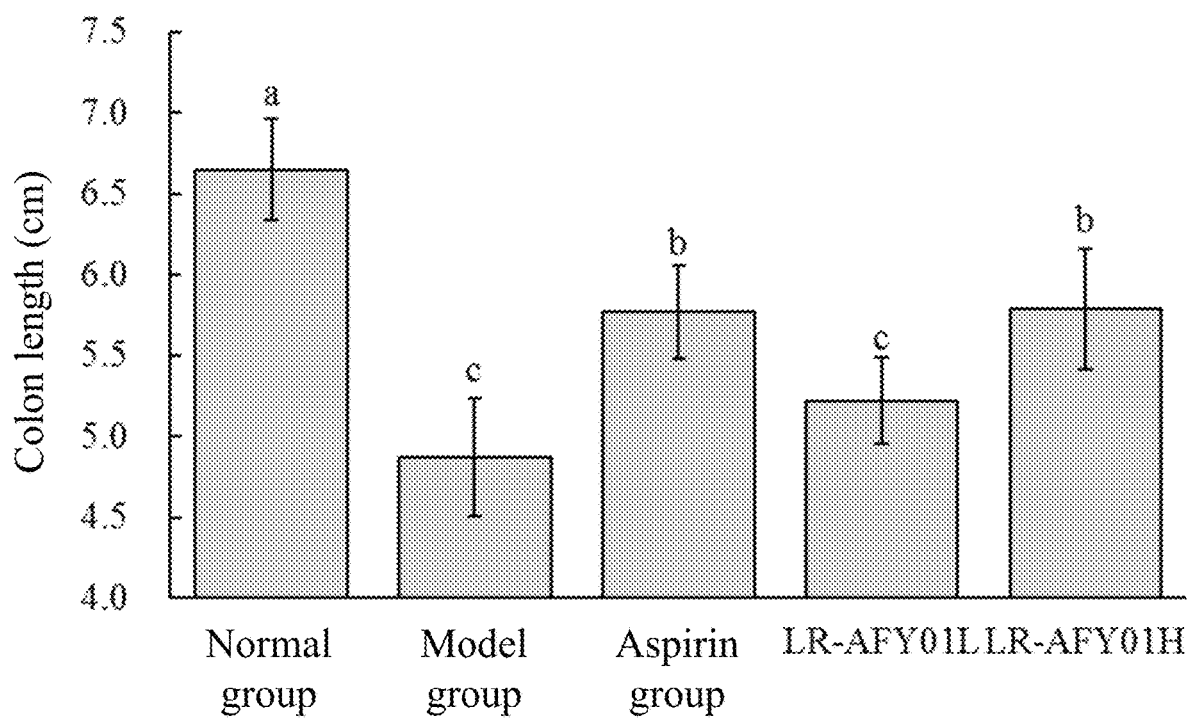
FIG. 4 shows influence of *Lacticaseibacillus rhamnosus* AFY01 on colon lengths of mice, where different lowercase letters mean significant difference (P<0.05), the same below.
Figure 5:
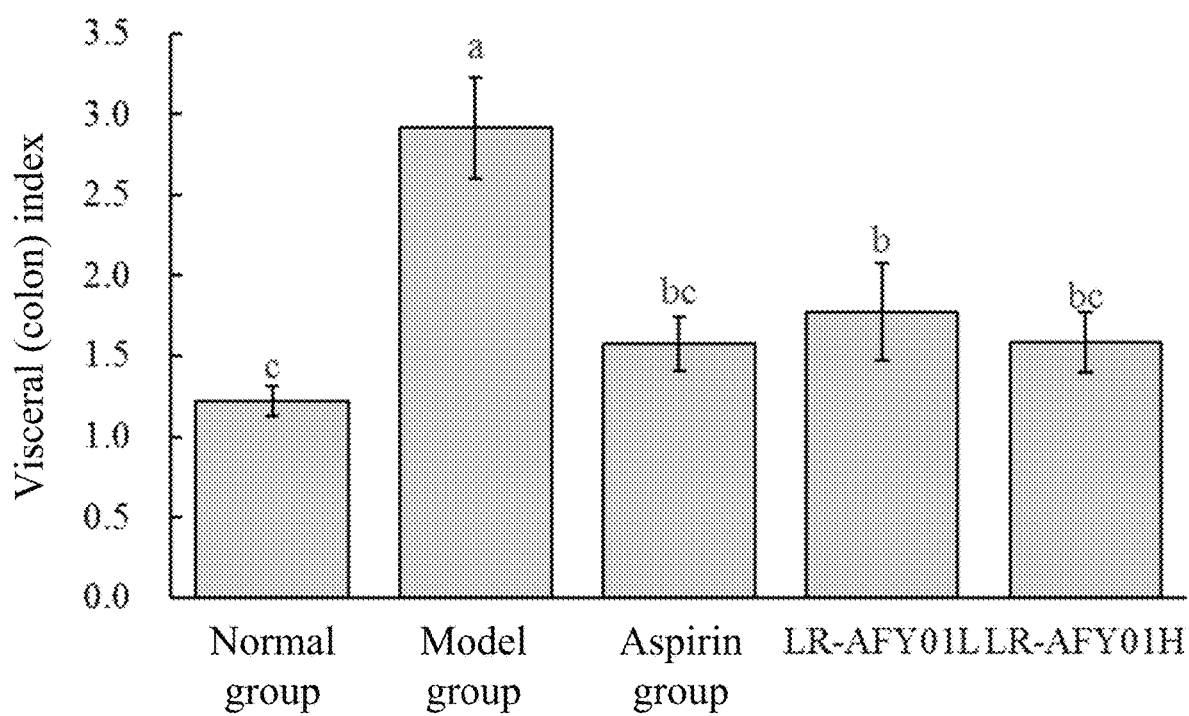
FIG. 5 shows influence of *Lacticaseibacillus rhamnosus* AFY01 on visceral (colon) indexes of mice.
Figure 6:
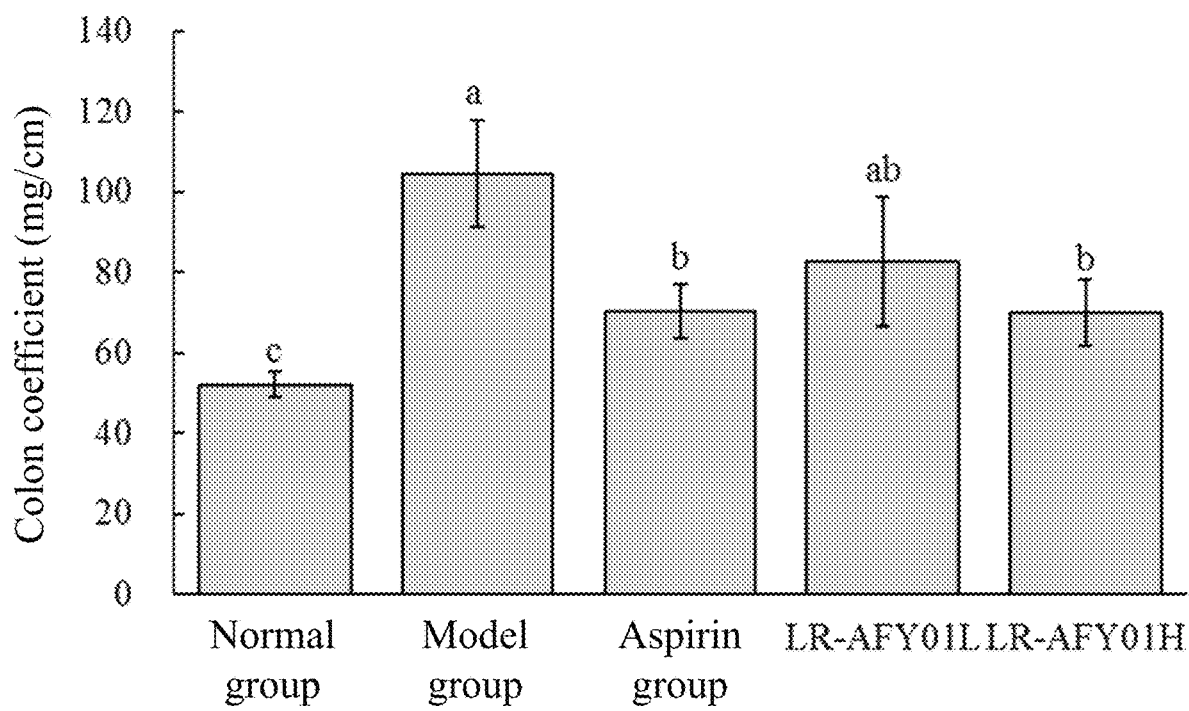
FIG. 6 shows influence of *Lacticaseibacillus rhamnosus* AFY01 on colon coefficients of mice.

2.5.2 Influence of LR-AFY01 on Colon Length, Visceral Index, Colon Coefficient and Intestinal Tumor in Mice As shown in FIG. 4, the colon length of mice in the normal group is 6.65±0.31 cm, the colon length of mice in the model group is 4.87±0.37 cm, the colon length of mice in the aspirin group is 5.77±0.29 cm, and the colon lengths of mice in LR-AFY01L and LR-AFY01H groups are 5.22±0.27 cm and 5.79±0.37 cm respectively. The colon length in the model group is shorter than that in the normal group (P<0.05), but LR-AFY01 can alleviate shortening of colon in mice, and results show significant difference (P<0.05). The effect of the LR-AFY01 is similar to that of the aspirin group. Meanwhile, FIGS. 5 and 6 show that the visceral (colon) index and the colon coefficient of the normal group, the aspirin group, the LR-AFY01H group and the LR-AFY01L group increase in turn, and are significantly lower than those of the model group (P<0.05)

Figure 7:
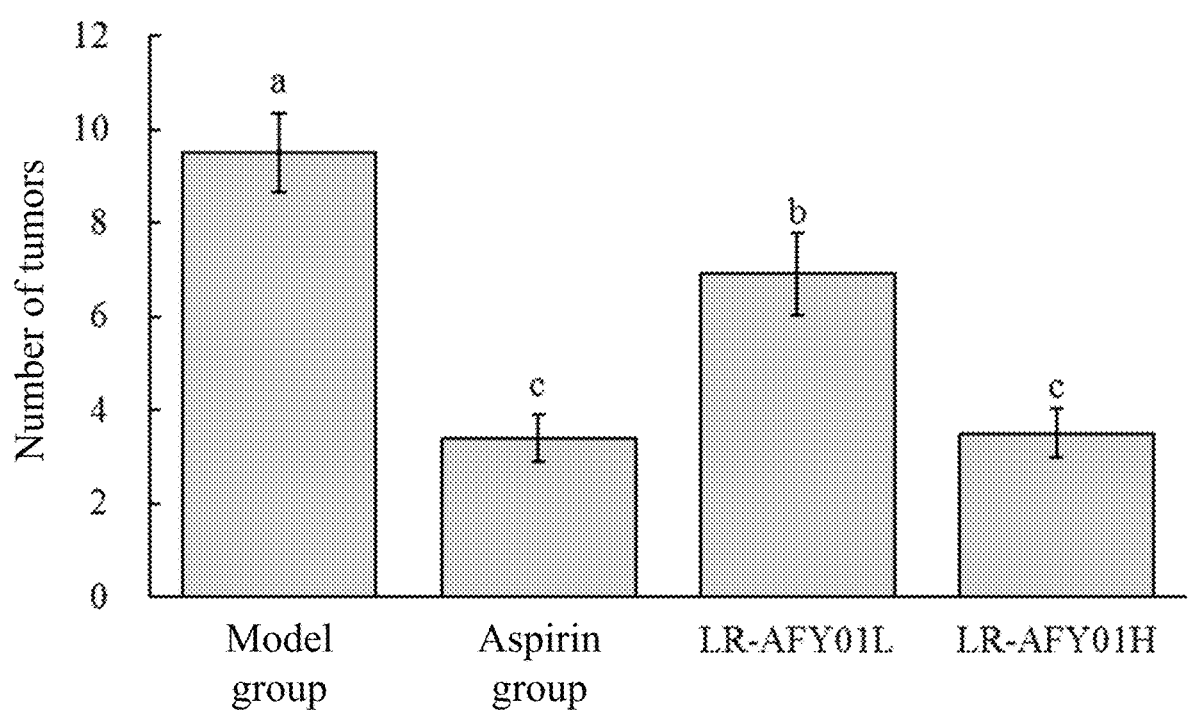
FIG. 7 shows influence of *Lacticaseibacillus rhamnosus* AFY01 on the number of colon tumors of mice.
Figure 8:
FIG. 8 shows a pathological influence of *Lacticaseibacillus rhamnosus* AFY01 on colon tissue of normal group mice.
Figure 9:
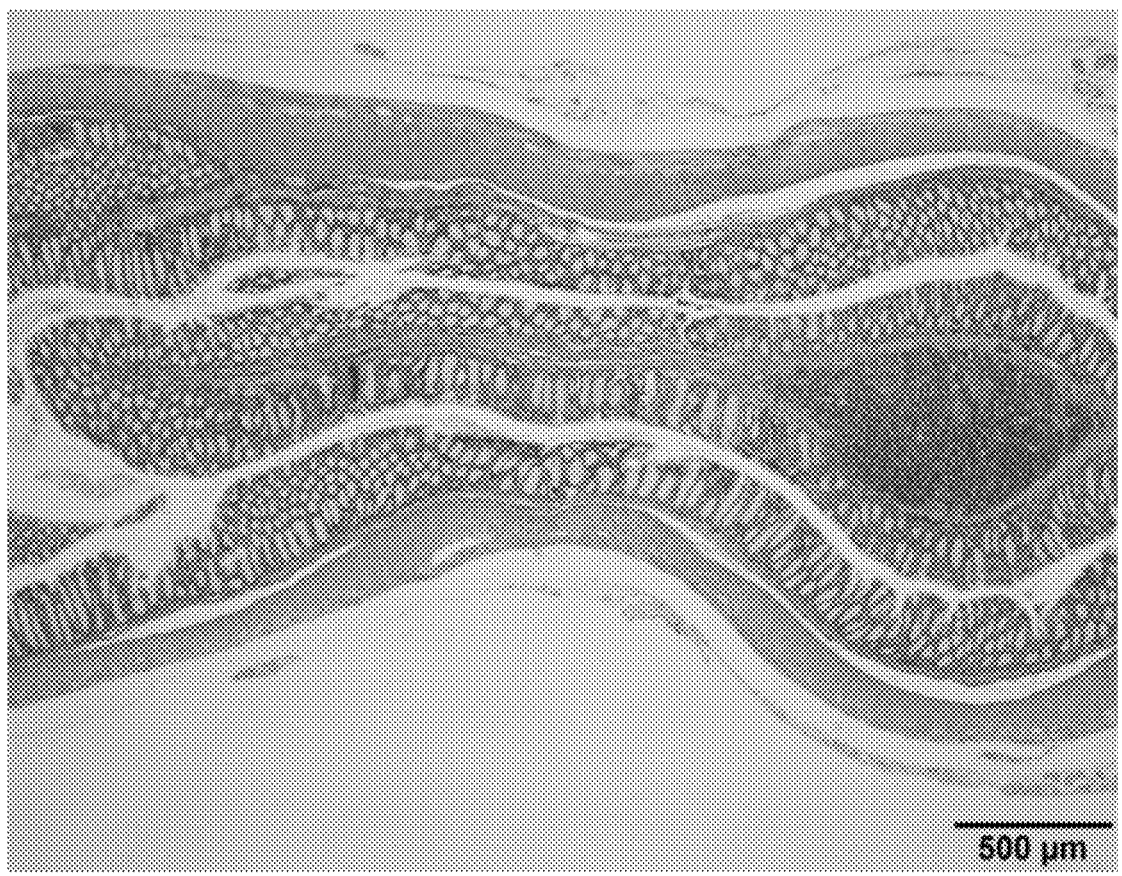
FIG. 9 shows a pathological influence of *Lacticaseibacillus rhamnosus* AFY01 on colon tissue of model group mice.
Figure 10:
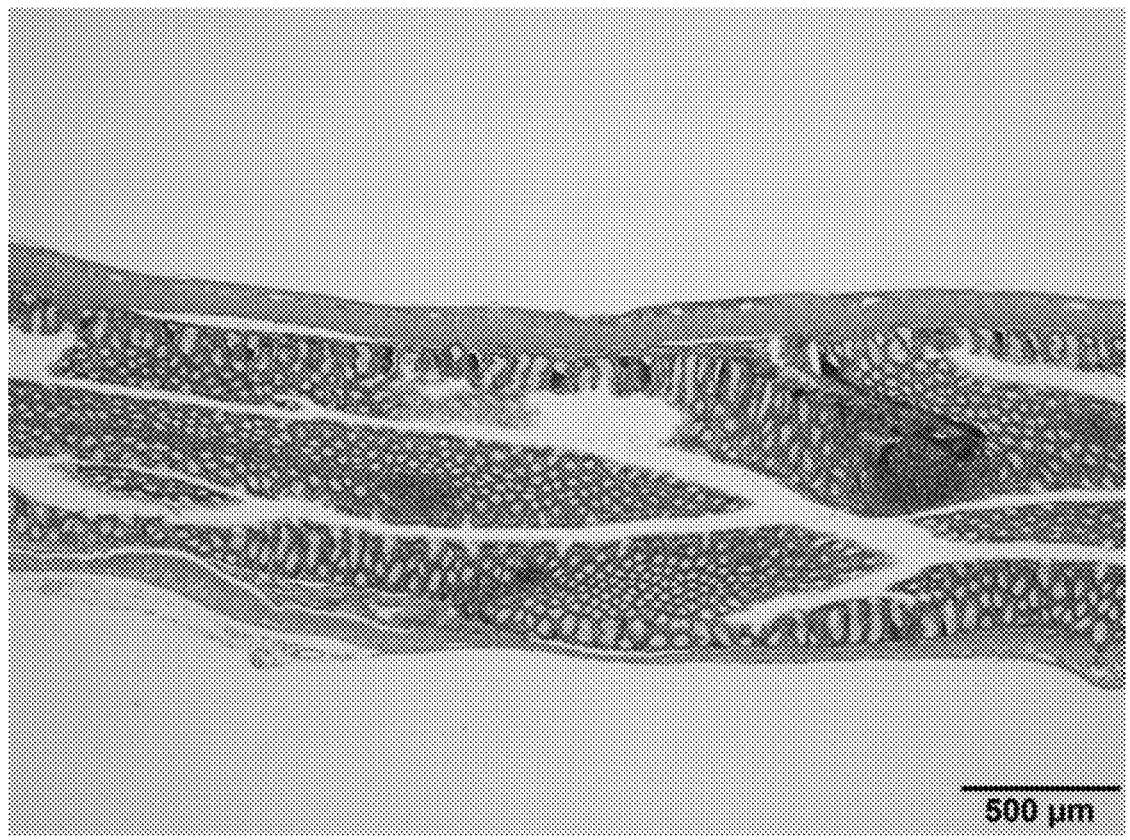
FIG. 10 shows a pathological influence of *Lacticaseibacillus rhamnosus* AFY01 on colon tissue of aspirin group mice.
Figure 11:
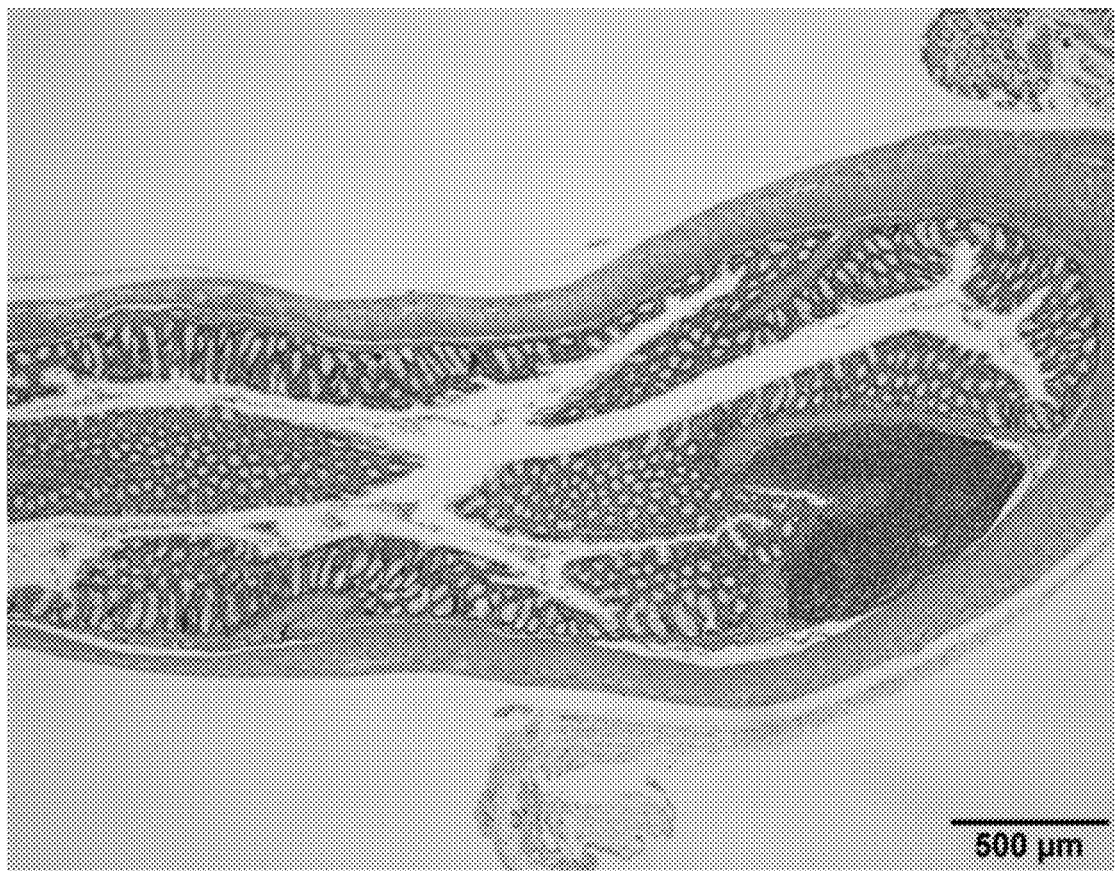
FIG. 11 shows a pathological influence of *Lacticaseibacillus rhamnosus* AFY01 on colon tissue of LR-AFY01L group mice.
Figure 12:
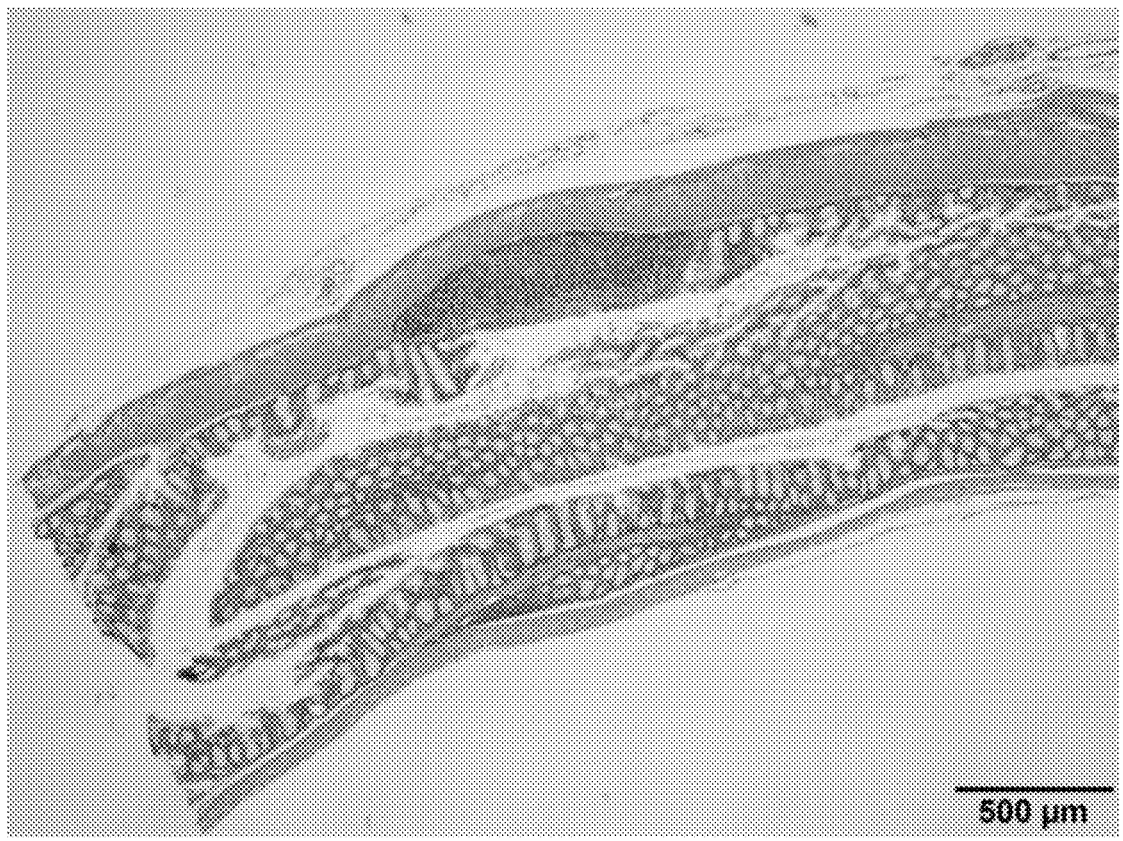
FIG. 12 shows a pathological influence of *Lacticaseibacillus rhamnosus* AFY01 on colon tissue of LR-AFY01H group mice.
Figure 13:
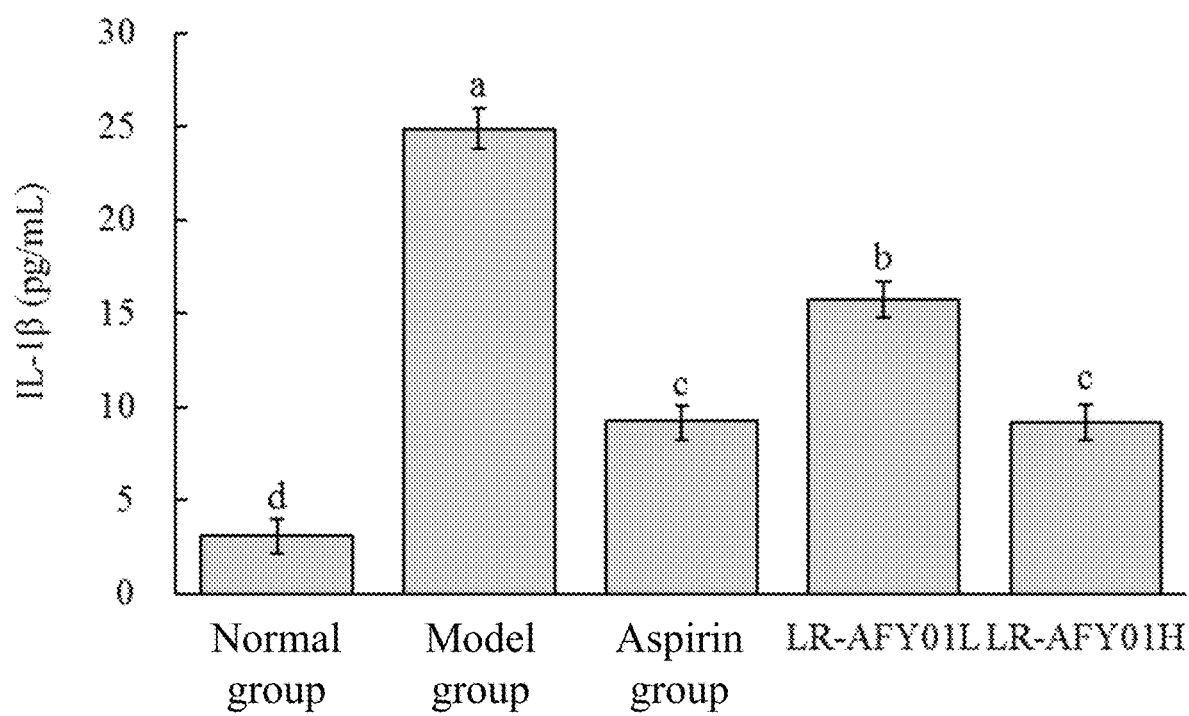
FIG. 13 shows influence of *Lacticaseibacillus rhamnosus* AFY01 on an inflammatory cytokine IL-1β in serum of mice.
Figure 14:
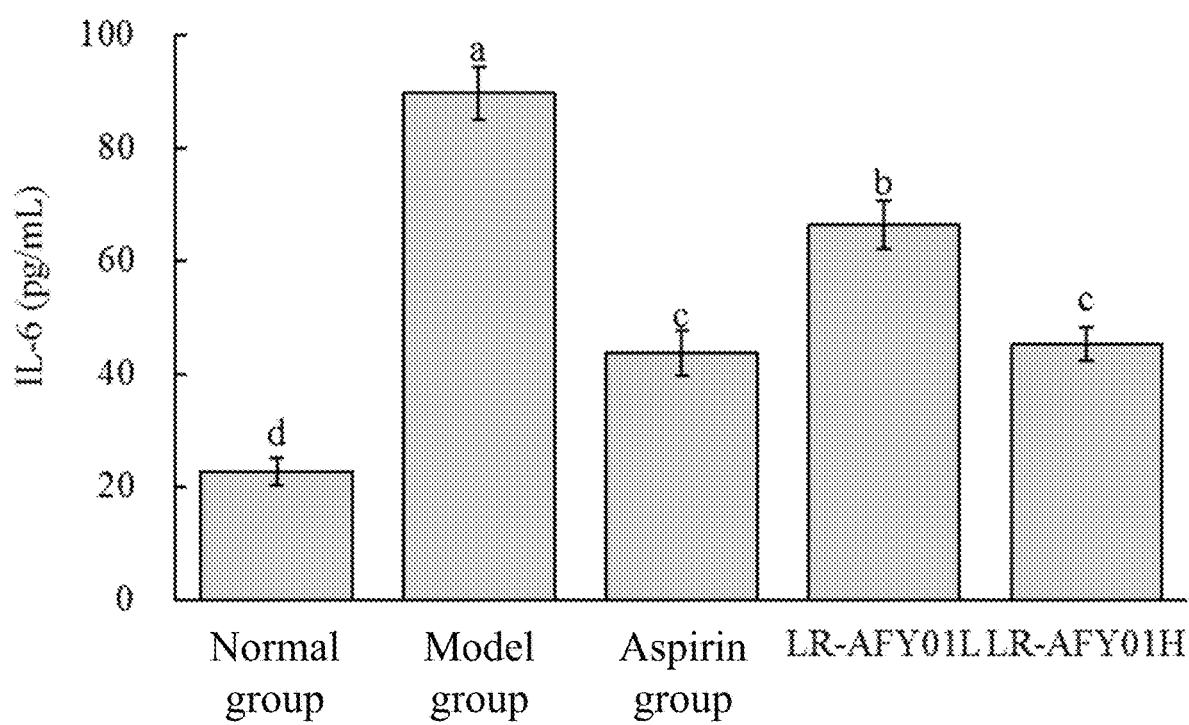
FIG. 14 shows influence of *Lacticaseibacillus rhamnosus* AFY01 on an inflammatory cytokine IL-6 in serum of mice.
Figure 15:
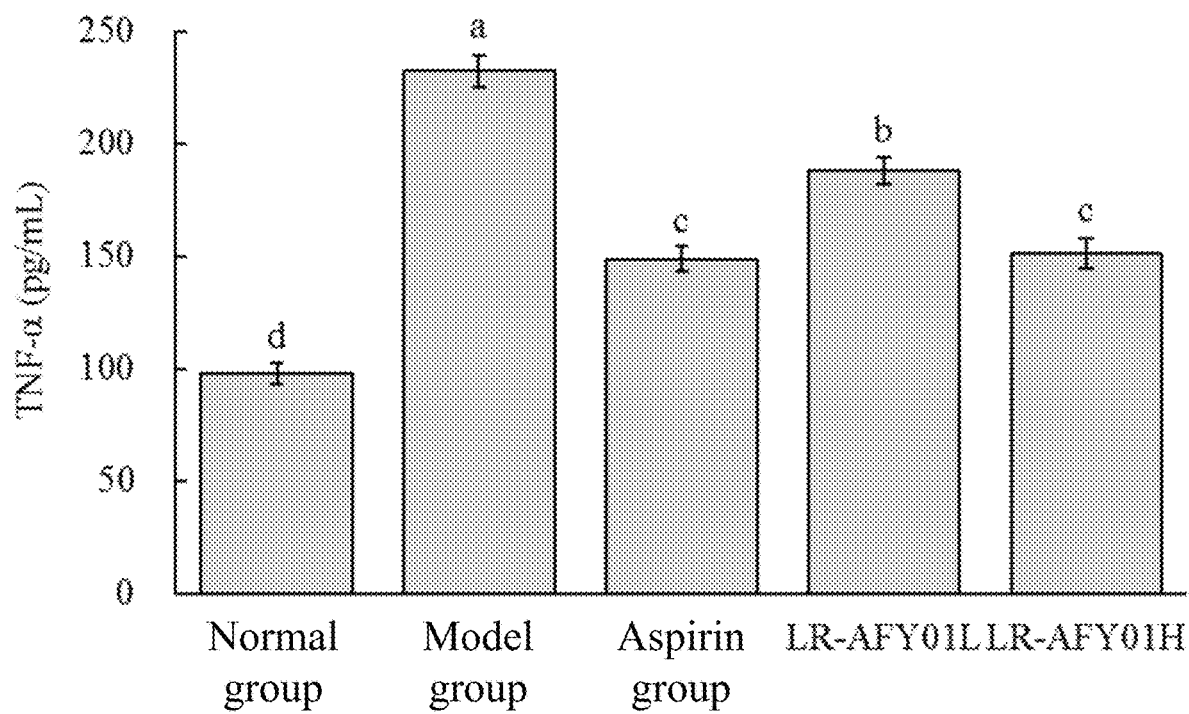
FIG. 15 shows influence of *Lacticaseibacillus rhamnosus* AFY01 on an inflammatory cytokine TNF-α in serum of mice.

FIG. 7 shows that no intestinal tumors are found in mice of the normal group, and several tumors of different sizes are seen in the colon segments of mice in the model group, aspirin group and LR-AFY01 groups. The model group has the most tumors (9.5±0.85), and the aspirin group, LR-AFY01L group and LR-AFY01H group have significantly fewer tumors, which are 3.4±0.52, 6.9±0.88 and 3.5±0.53 respectively. Therefore, the LR-AFY01 can effectively relieve colon shortening caused by intestinal inflammation edema, reduce colon coefficients of the mice, and reduce visceral indexes and intestinal tumor occurrence of the mice.

2.5.3 Pathological Influence of LR-AFY01 on Colon Tissue of Mice

H&E staining analysis (FIGS. 8-12) shows that in the normal group, mucosal epithelial cells of colon tissue of mice are complete, crypts are normal, glands are arranged neatly, and there is no ulcer. In the model group, the intestinal tracts of mice are infiltrated by a large number of inflammatory cells, and multiple necrotic lesions and crypt abscesses appear. In the aspirin group, the infiltration degree of inflammatory cells is relatively low, and the crypt structure is less damaged. The LR-AFY01 groups show slight inflammatory infiltration, but the crypt structure is relatively intact. Compared with low-concentration LR-AFY01, high-concentration LR-AFY01 improves the pathological damage of the colon tissue caused by AOM/DSS to a greater extent.

2.5.4 Influence of LR-AFY01 on Levels of Inflammatory Cytokines in Serum and Colon Tissue of Mice In the disclosure, whether the antitumor activity of LR-AFY01 is related to the expression of proinflammatory cytokines is evaluated, and the expression levels of IL-1β, IL-6, TNF-α, NF-κB and iNOS in serum and colon tissue of mice are analyzed through ELISA experiments. According to FIGS. 13-15 and FIGS. 18-20, after AOM/DSS modeling, the levels of IL-1β, IL-6 and TNF-α in serum and colons of mice in the model group are significantly increased, aspirin and LR-AFY01 can effectively reduce the expression of these cytokines, and the levels of IL-1β, IL-6 and TNF-α in serum of the LR-AFY01H group are significantly lower than those of LR-AFY01L group (P<0.05), indicating that LR-AFY01 with a high concentration can significantly reduce the levels of proinflammatory cytokines in serum of mice with colon cancer.

Figure 16:
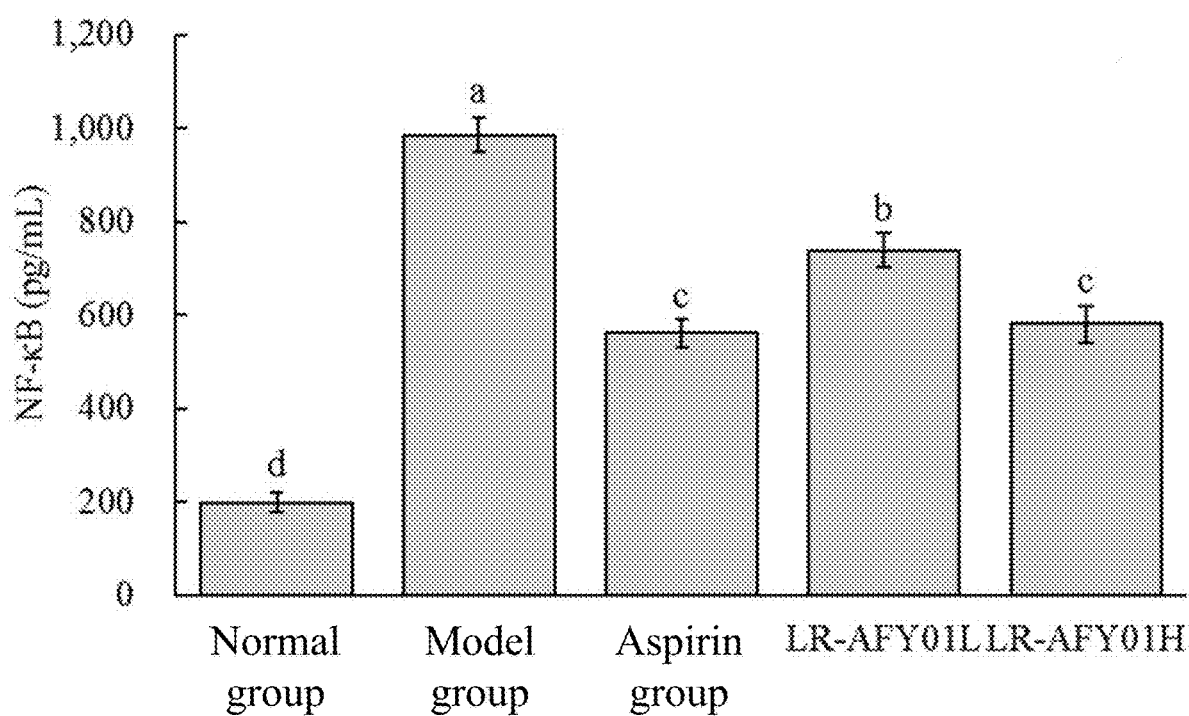
FIG. 16 shows influence of *Lacticaseibacillus rhamnosus* AFY01 on an inflammatory cytokine NF-κB in serum of mice.
Figure 17:
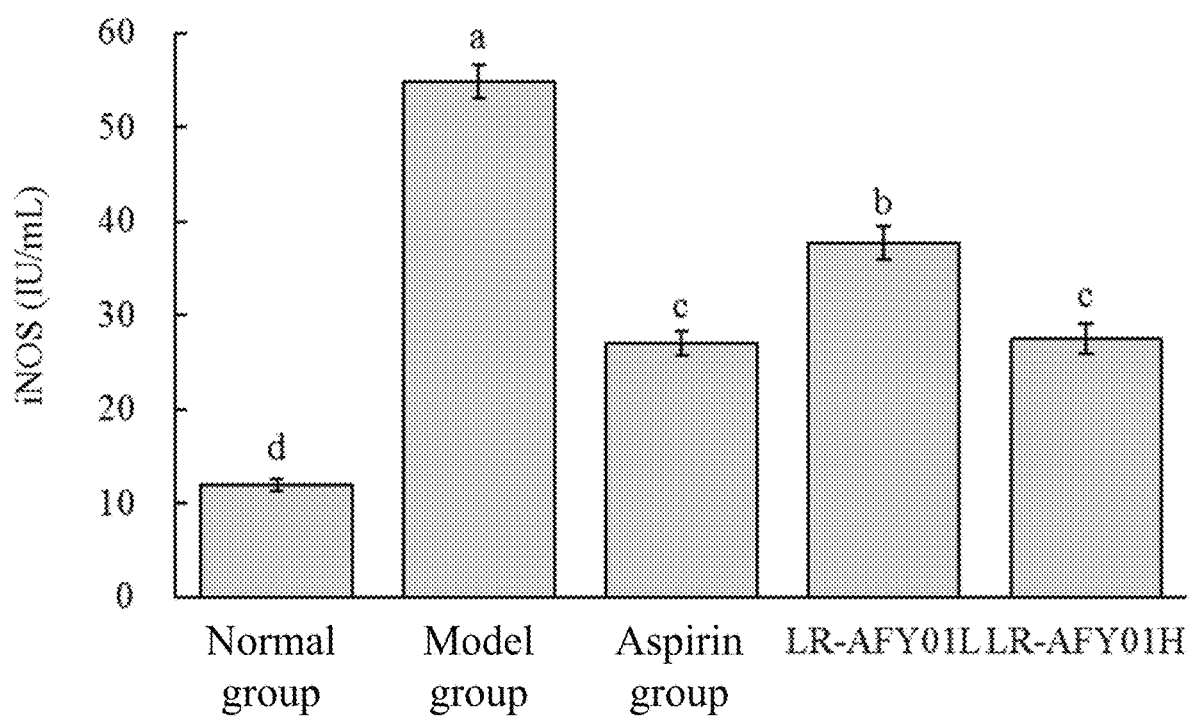
FIG. 17 shows influence of *Lacticaseibacillus rhamnosus* AFY01 on an inflammatory cytokine iNOS in serum of mice.
Figure 18:
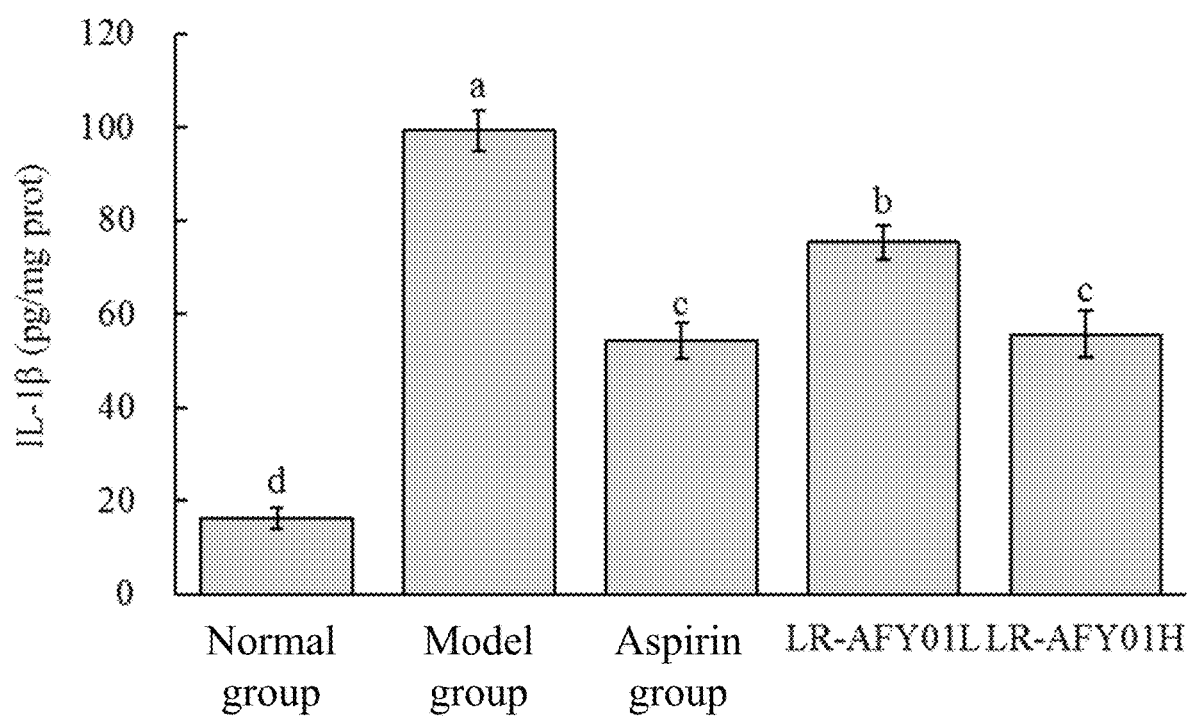
FIG. 18 shows influence of *Lacticaseibacillus rhamnosus* AFY01 on an inflammatory cytokine IL-1β in colons of mice.
Figure 19:
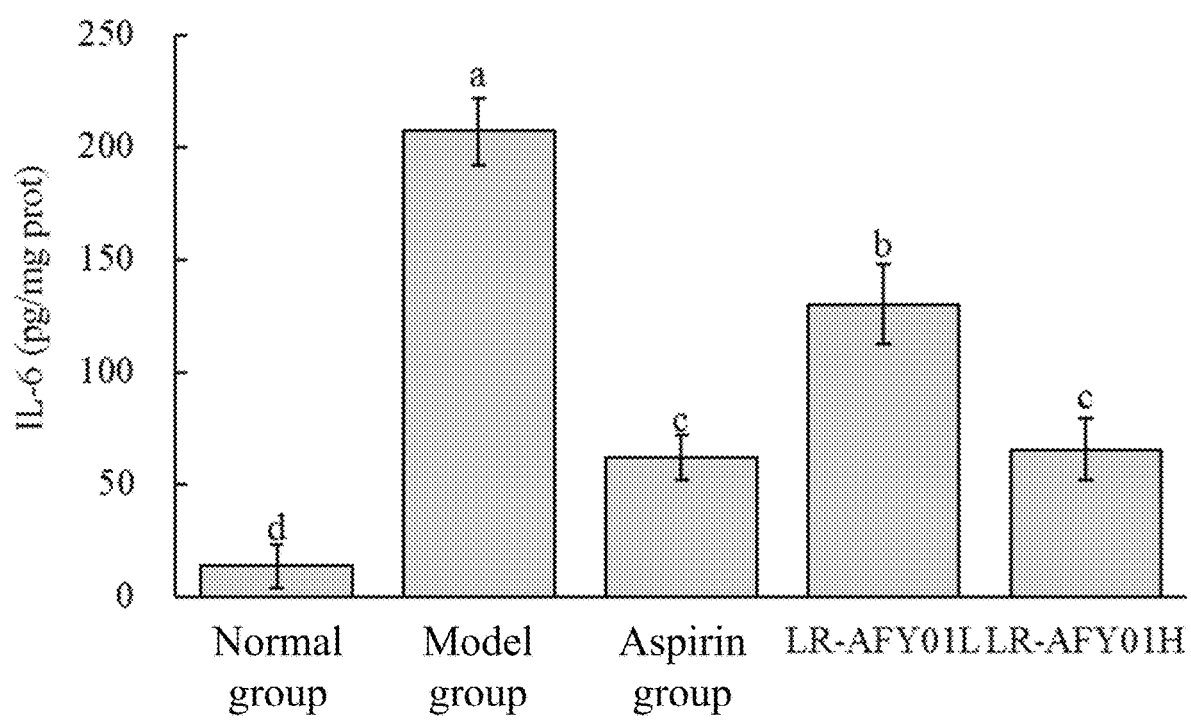
FIG. 19 shows influence of *Lacticaseibacillus rhamnosus* AFY01 on an inflammatory cytokine IL-6 in colons of mice.
Figure 20:
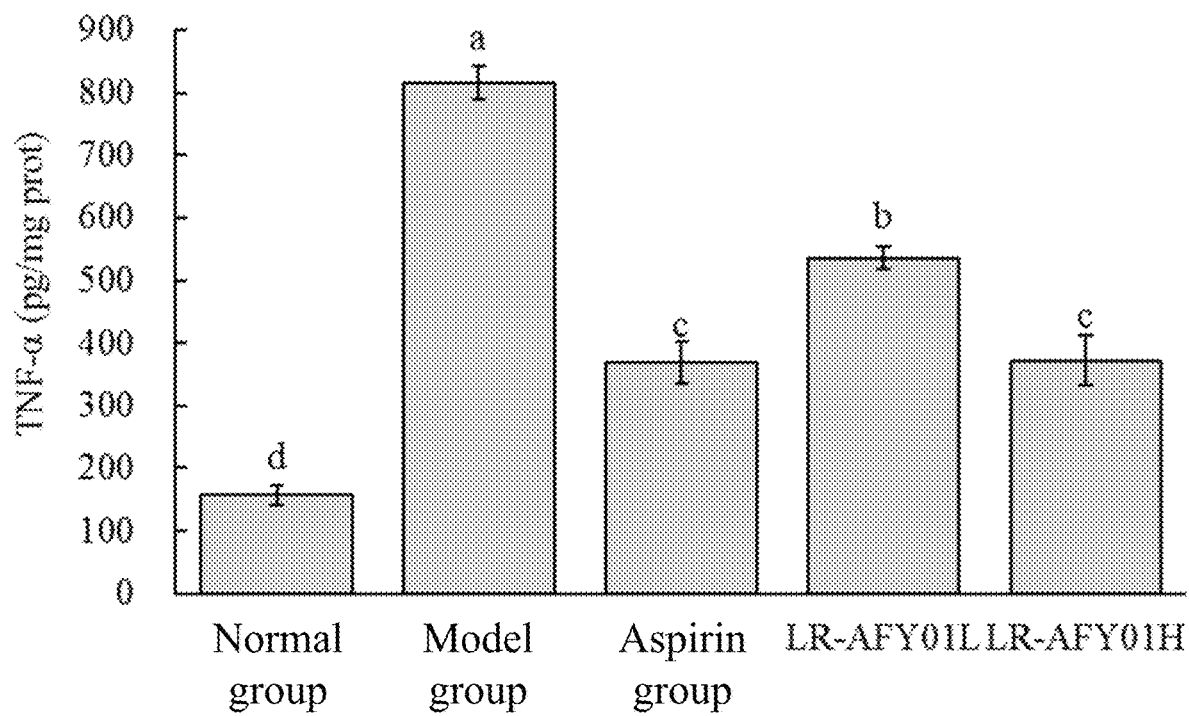
FIG. 20 shows influence of *Lacticaseibacillus rhamnosus* AFY01 on an inflammatory cytokine TNF-α in colons of mice.
Figure 21:
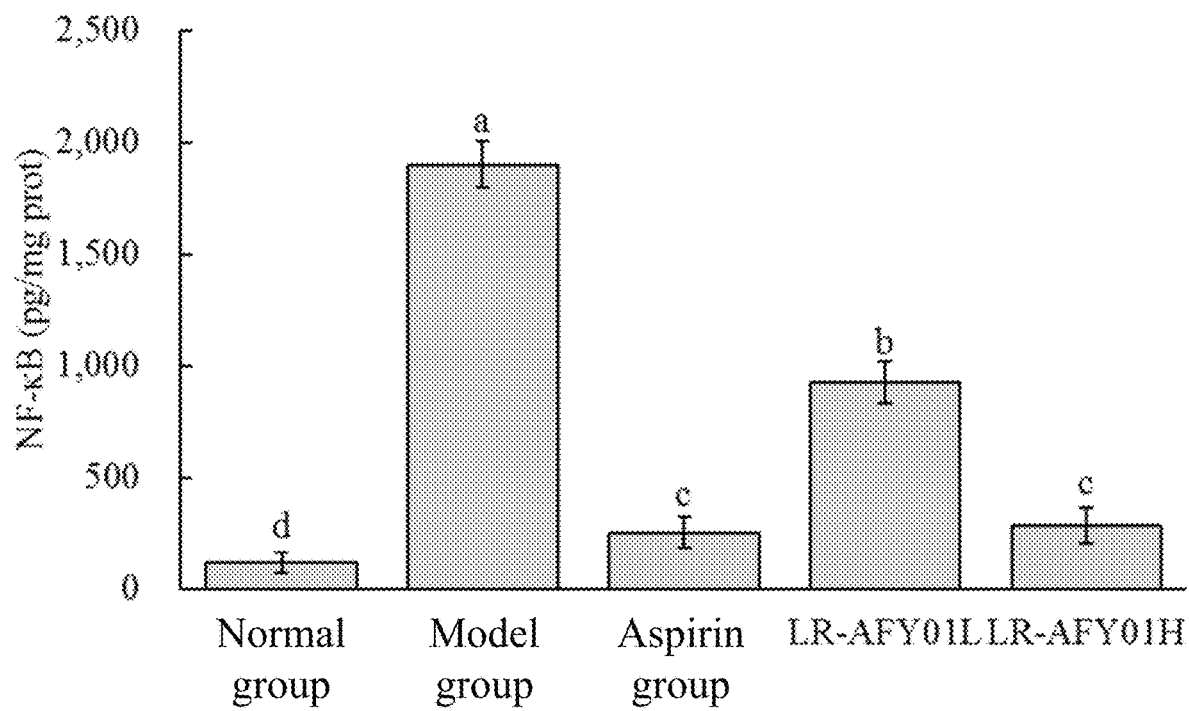
FIG. 21 shows influence of *Lacticaseibacillus rhamnosus* AFY01 on an inflammatory cytokine NF-κB in colons of mice.
Figure 22:
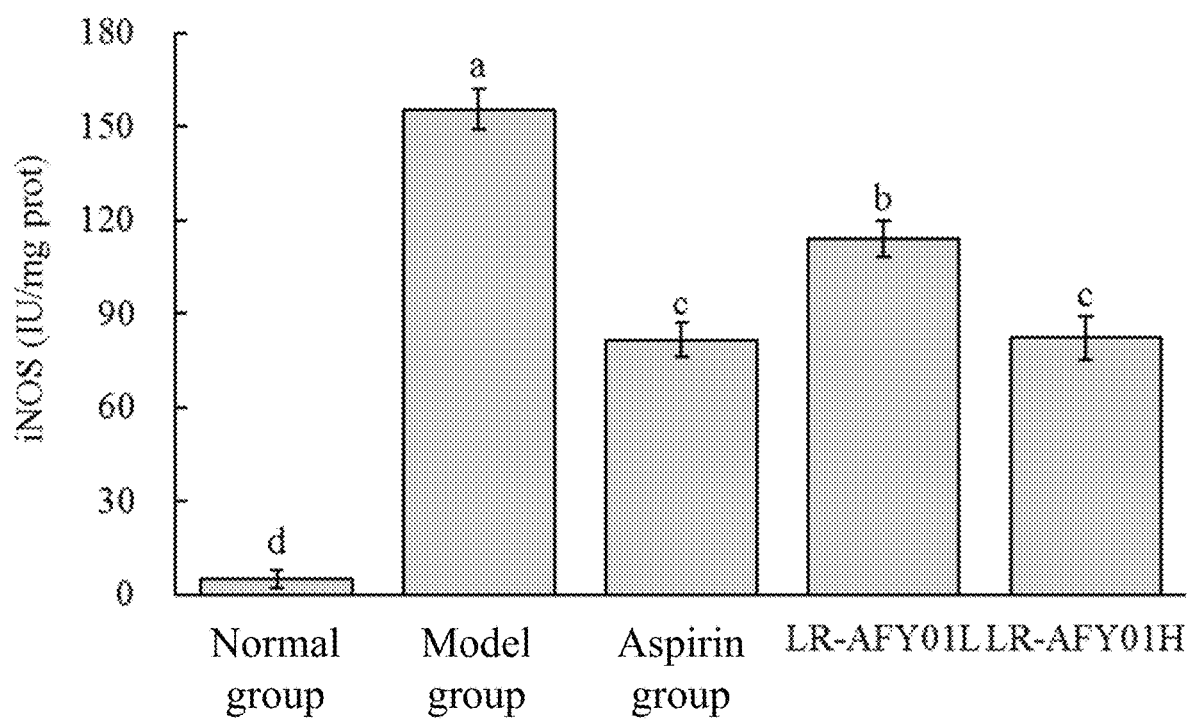
FIG. 22 shows influence of *Lacticaseibacillus rhamnosus* AFY01 on an inflammatory cytokine iNOS in colons of mice.
Figure 23:
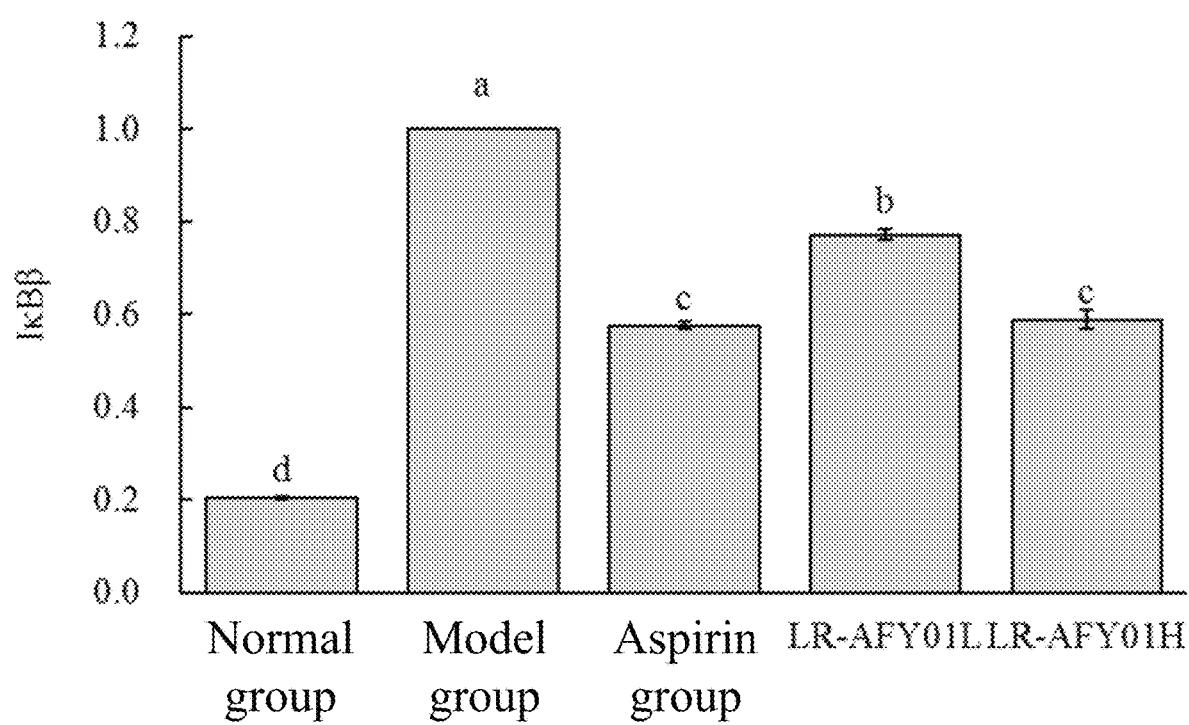
FIG. 23 shows influence of *Lacticaseibacillus rhamnosus* AFY01 on a relative expression level of an inflammatory factor IκBβ in colon tissue of mice.
Figure 24:
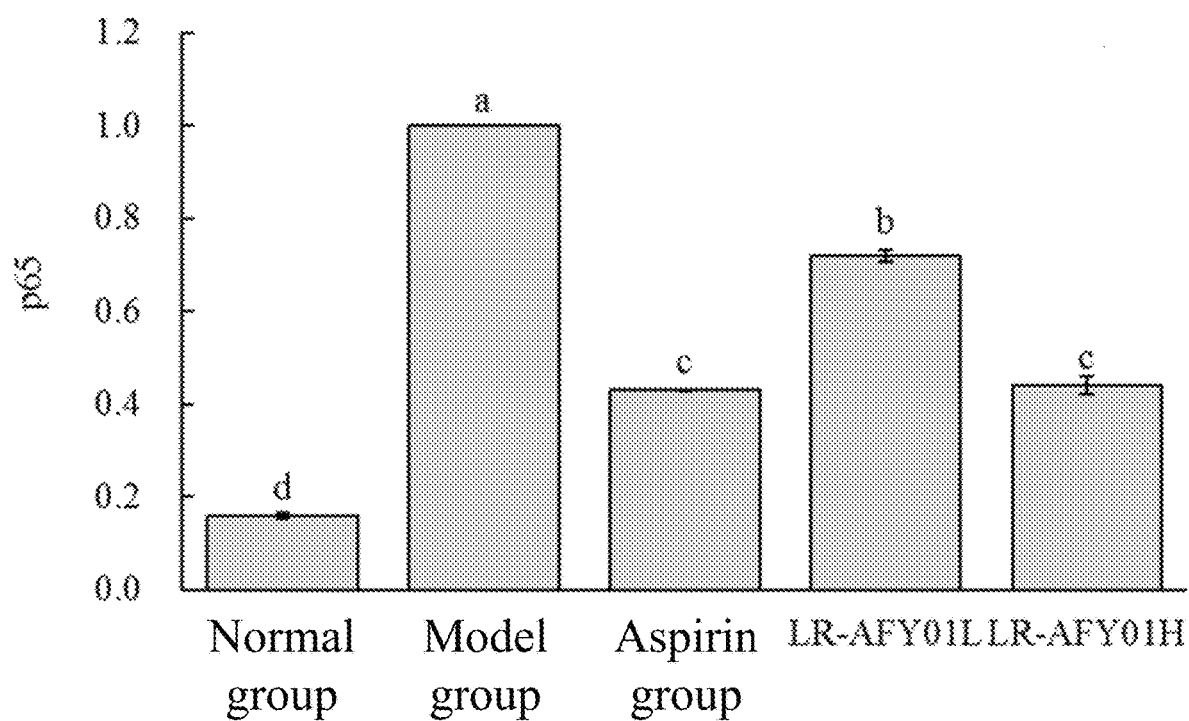
FIG. 24 shows influence of *Lacticaseibacillus rhamnosus* AFY01 on a relative expression level of an inflammatory factor p65 in colon tissue of mice.
Figure 25:
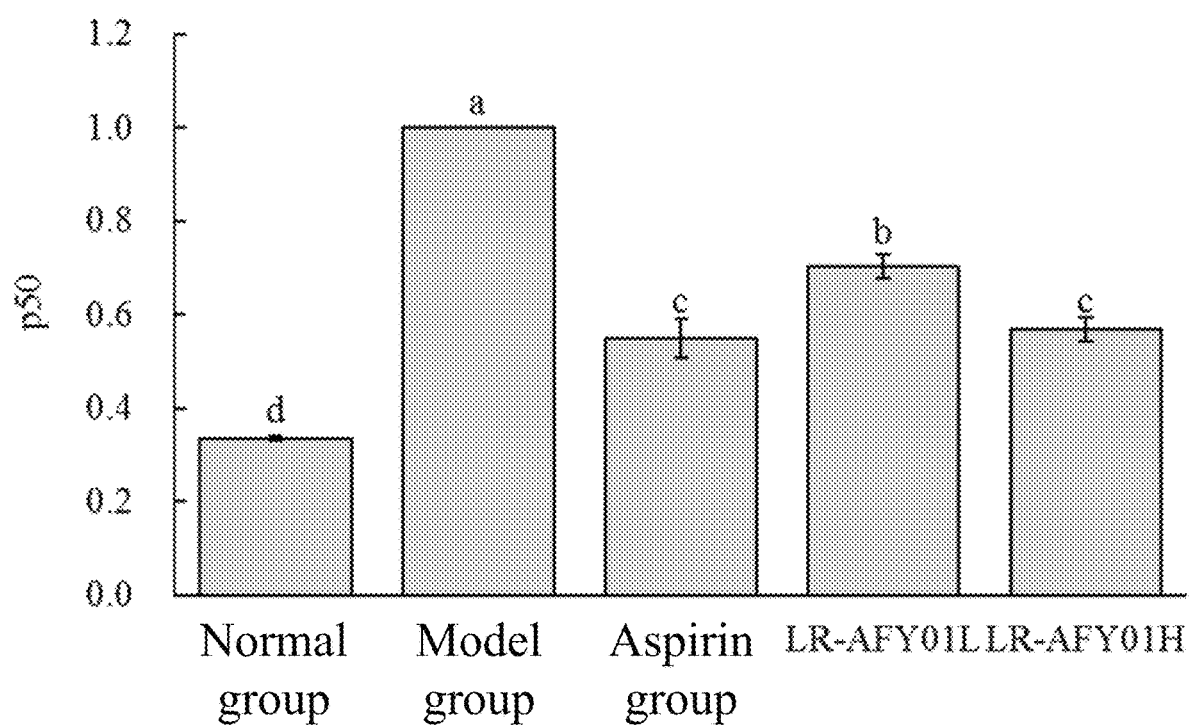
FIG. 25 shows influence of *Lacticaseibacillus rhamnosus* AFY01 on a relative expression level of an inflammatory factor p50 in colon tissue of mice.
Figure 26:
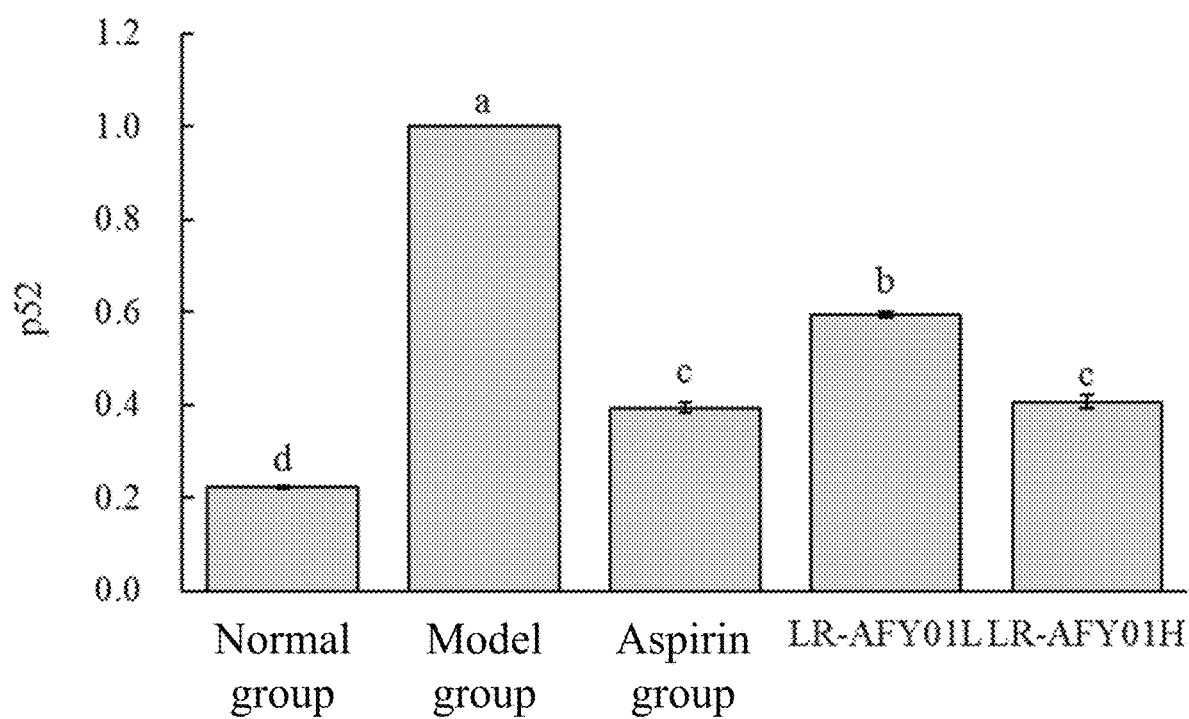
FIG. 26 shows influence of *Lacticaseibacillus rhamnosus* AFY01 on a relative expression level of an inflammatory factor p52 in colon tissue of mice.

FIG. 16 and FIG. 21 show that the concentrations of NF-κB in serum and colon tissue of mice in the model group are the highest, and the concentrations in serum of mice in the normal group, the aspirin group and the LR-AFY01 groups are lower than those in the model group, and there is significant difference (P<0.05). FIG. 17 and FIG. 22 show that iNOS is highly expressed in serum and colon tissue of mice in the model group. The concentrations of iNOS in serum of mice in the normal group, the aspirin group and the LR-AFY01 groups are lower than those of the model group, and there is significant difference (P<0.05). Data disclosed in the disclosure reveal that the treatment with AOM/DSS can induce high expression of proinflammatory cytokines and nitric oxide synthase in mice, and activate the NF-kappa B inflammatory pathway at the same time, causing continuous inflammatory response in the body. However, intragastric administration of LR-AFY01 of experimental strains can effectively reduce the levels of the proinflammatory cytokines (IL-1β, IL-6 and TNF-α) in mice with colon cancer, perform down regulation on the expression of NF-κB and iNOS, and alleviate the pathological state of inflammation. Results of serum and colon tissue of mice are consistent.

2.5.5 Influence of LR-AFY01 on mRNA Expression Levels of Inflammatory Pathway-Related Factors in Colon Tissue of Mice In the disclosure, real-time fluorescence quantitative PCR is used for analyzing mRNA expression levels of IκBβ, p65, p50 and p52 in colon tissue of mice, and results show (FIGS. 23-26) that the mRNA expression levels of IκBβ, p65, p50 and p52 in colon tissue of mice are the highest in model group, which are significantly decreased in the aspirin group and the LR-AFY01 groups (P<0.05), and the effect of the high-concentration LR-AFY01 group is similar to the effect of aspirin.

Figure 27:
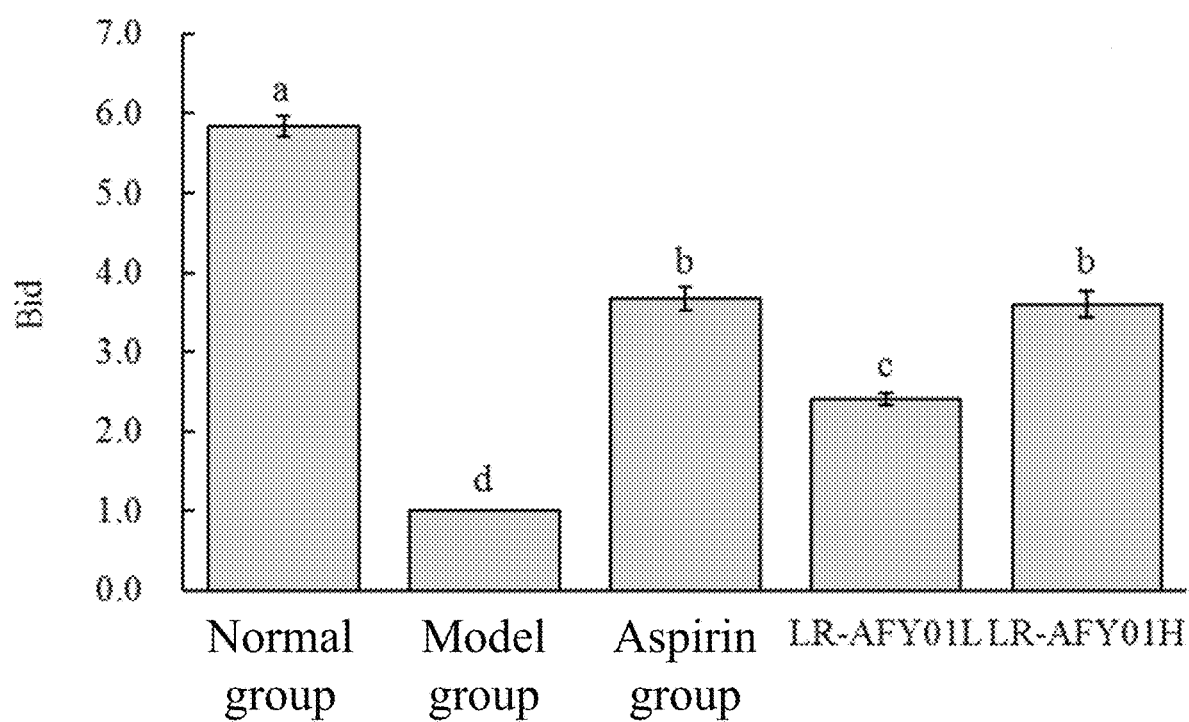
FIG. 27 shows influence of *Lacticaseibacillus rhamnosus* AFY01 on a relative expression level of an apoptosis-related factor Bid in colon tissue of mice.
Figure 28:
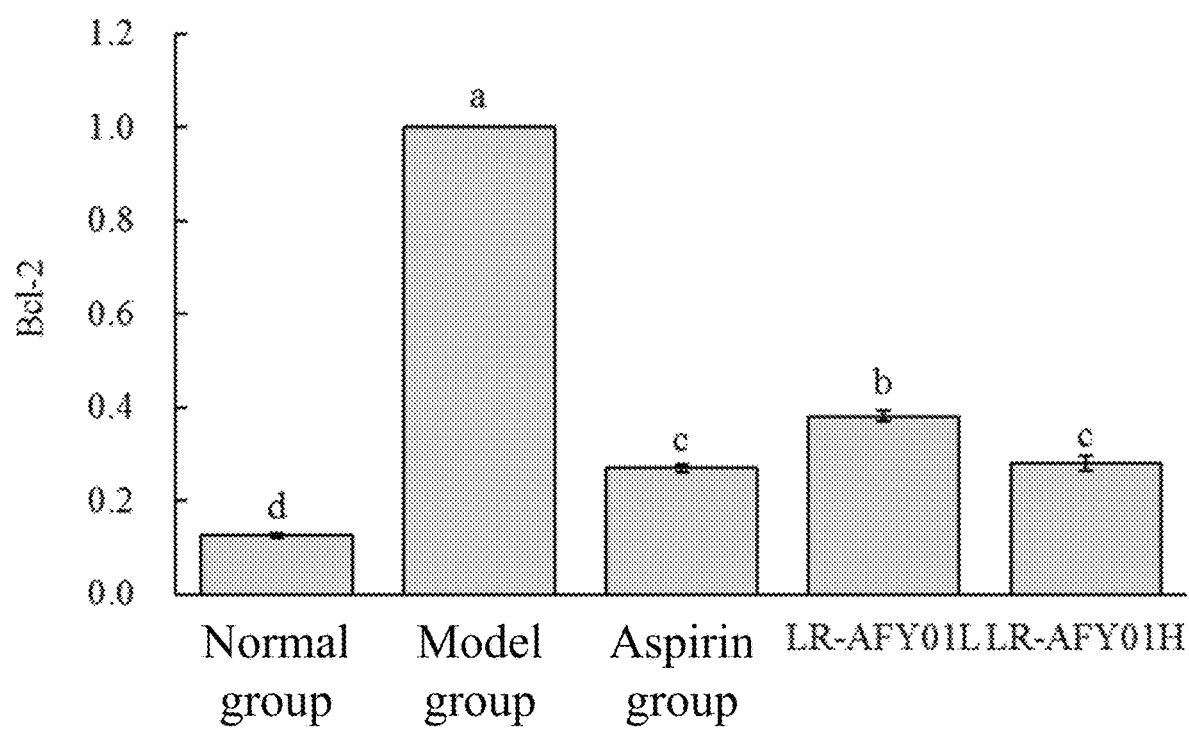
FIG. 28 shows influence of *Lacticaseibacillus rhamnosus* AFY01 on a relative expression level of an apoptosis-related factor Bcl-2 in colon tissue of mice.
Figure 29:
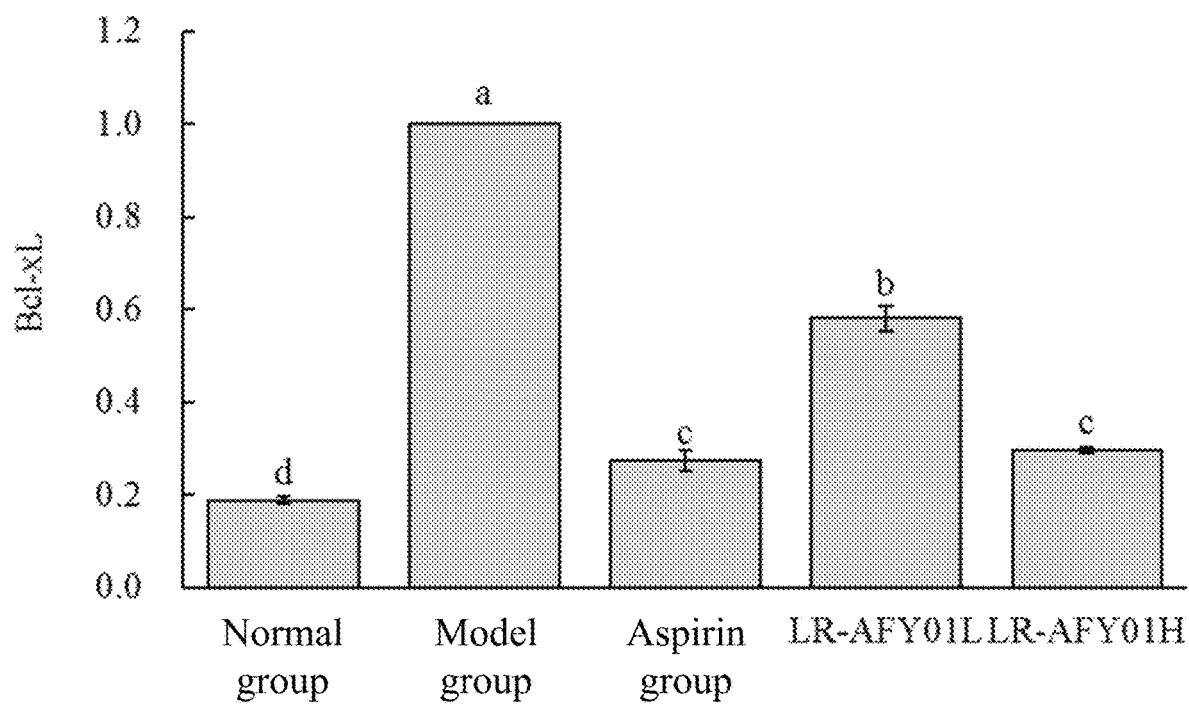
FIG. 29 shows influence of *Lacticaseibacillus rhamnosus* AFY01 on a relative expression level of an apoptosis-related factor Bcl-xL in colon tissue of mice.
Figure 30:
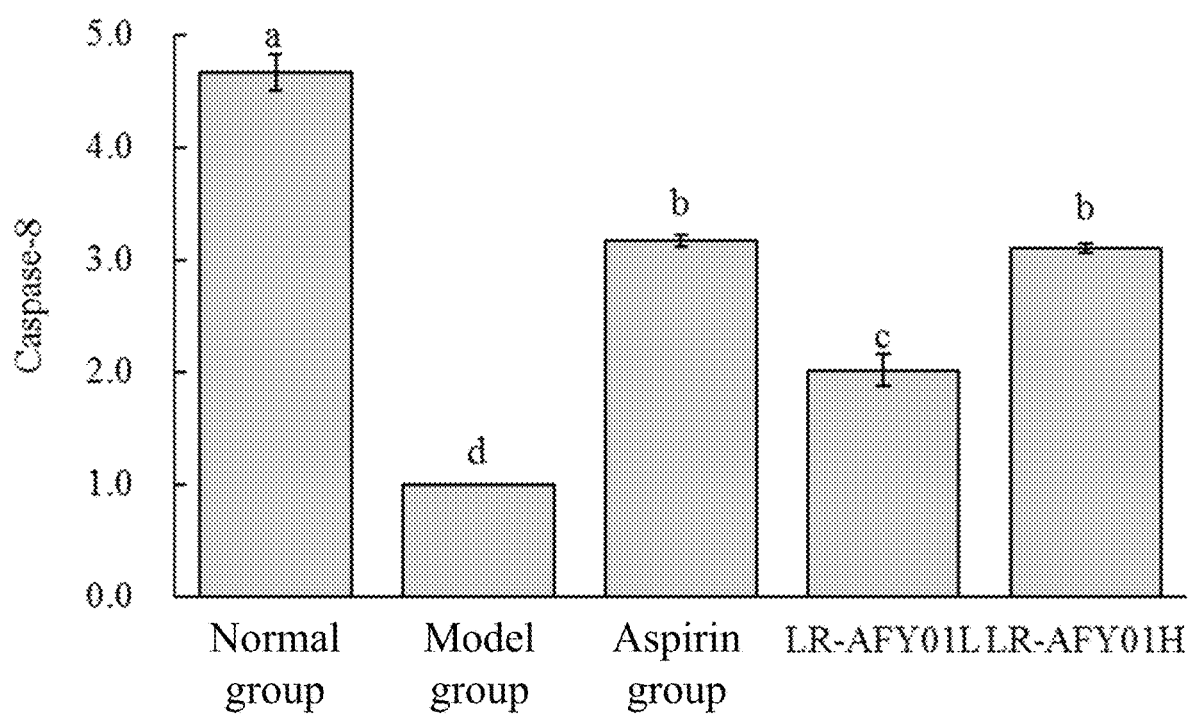
FIG. 30 shows influence of *Lacticaseibacillus rhamnosus* AFY01 on a relative expression level of an apoptosis-related factor caspase-8 in colon tissue of mice.

2.5.6 Influence of LR-AFY01 on mRNA Expression Levels of Apoptosis Pathway-Related Factors in Colon Tissue of Mice FIG. 27 shows that compared with the normal group, the pro-apoptotic factor Bid is expressed at a low level in the model group, the relative expression levels in the aspirin group and the LR-AFY01 groups are increased, and the difference is significant (P<0.05). Meanwhile, FIGS. 28 and 29 show that anti-apoptotic factors Bcl-2 and Bcl-$x_L$ are highly expressed in the model group, while the expression in the aspirin group and the LR-AFY01 groups is significantly reduced (P<0.05). As FIG. 30 shows, compared with the normal group, the relative mRNA expression level of caspase-8 in colon tissue of mice in the model group is significantly reduced (P<0.05) under induction of AOM/DSS, while aspirin and LR-AFY01 intervention can significantly improve the low mRNA expression of caspase-8 caused by cancer in mice, and compared with the model group, the mRNA levels of caspase-8 in the high-concentration and low-concentration LR-AFY01 groups are significantly different (P<0.05). The present experimental results indicate that LR-AFY01 can significantly improve the expression of the pro-apoptotic factors Bid and caspase-8, while decreasing the expression of the anti-apoptotic factors Bcl-2 and Bcl-xL.

2.6 Conclusion

In this experiment, deep studies are carried out on the effect and mechanism of action of LR-AFY01 isolated from Xinjiang fermented yogurt on intervention of inflammatory colon cancer through an AOM/DSS-induced mouse inflammation-associated colon cancer model from the following five aspects: weight and visceral index, colon index and intestinal tumor number, histopathological analysis of colon tissue, analysis of inflammatory cytokines in serum and colon tissue, and analysis of NF-κB and apoptosis signal pathway related gene expression in colon tissue. Experimental results show that LR-AFY01 significantly relieves the weight loss, visceral index increase, colon shortening and intestinal index increase caused by cancer in mice, effectively reduces the incidence of intestinal tumors in mice with cancer, and alleviates the pathological damage of the colon tissue (P<0.05). Moreover, LR-AFY01 intervention significantly decreases the expression levels of inflammatory cytokines IL-1β, IL-6, TNF-α, NF-κB and iNOS in serum and colon tissue of mice (P<0.05). In addition, LR-AFY01 can also perform significant down regulation on the mRNA expression of proinflammatory factors IκBβ, p65, p50 and p52, and anti-apoptotic factors Bcl-2 and Bcl-$x_L$, and perform significant up regulation on the mRNA expression of pro-apoptotic factors Bid and caspase-8 (P<0.05). This study suggests for the first time that LR-AFY01 plays a significant role in interfering with the development of inflammation-related colon cancer in mice, and reveals the specific mechanism of slowing down the development of colon cancer by relieving intestinal inflammation and promoting apoptosis of intestinal tumor cells, thereby providing scientific evidence for the health function of LR-AFY01 on the intestinal tract, and providing more scientific basis for prevention and adjuvant treatment of colon cancer from diet. Further studies may be carried out from clinical aspects in the future.

Comparative Example

The expression levels of apoptosis pathway-related genes Bcl-2 and Bcl-$x_L$ in colon tissue of mice are determined according to the experimental method of 2.3 in Embodiment 2, and the following comparative example is set up. The difference between the comparative example and Embodiment 2 and testing results are shown in Table 3 below:

TABLE 3

| | Difference from Embodiment 2 | Relative mRNA expression level of Bcl-2 | Relative mRNA expression level of Bcl-$x_L$ |
|---|---|---|---|
| Comparative Example | Replace the high-concentration LR-AFY01 (LR-AFY01H) group with equal amount of *Lacticaseibacillus rhamnosus* AFY05 (CGMCC No. 27365) | 0.729 ± 0.023 | 0.738 ± 0.029 |

The above results show that down regulation degree of the relative mRNA expression levels of Bcl-2 and Bcl-$x_L$ in colon tissue of mice interfered by *Lacticaseibacillus rham-*

*nosus* AFY05 (CGMCC No. 27365) is not as high as that in the high-concentration LR-AFY01 (LR-AFY01H) group, and the relative mRNA expression levels of Bcl-2 and Bcl-$x_L$ are significantly higher than those in the low-concentration LR-AFY01 (LR-AFY01L) group of the disclosure.

What is claimed is:

1. A culture method for *Lacticaseibacillus rhamnosus* AFY01 with a preservation number of CGMCC No. 27362 comprising inoculating the *Lacticaseibacillus rhamnosus* AFY01 with a preservation number of CGMCC No. 27362 onto a culture medium for culture, wherein the culture medium comprises a De Man, Rogosa and Sharpe (MRS) culture medium.

2. The culture method for the *Lacticaseibacillus rhamnosus* AFY01 with a preservation number of CGMCC No. 27362 according to claim 1, wherein a temperature of the culture is 37° C., and a time of the culture is in a range of 18 hours to 24 hours.

* * * * *